(12) United States Patent
Back et al.

(10) Patent No.: US 12,122,838 B2
(45) Date of Patent: *Oct. 22, 2024

(54) HUMANIZED ANTI-CCR7 RECEPTOR ANTIBODIES

(71) Applicant: PepMab B.V., Lelystad (NL)

(72) Inventors: Jaap Willem Back, Vleuten (NL);
Ronald Boshuizen, Spanga (NL);
Wouter Cornelis Puijk, Lelystad (NL);
Johan Turkstra, Dronten (NL); Klaus Heinrich Schwamborn, Nantes (FR)

(73) Assignee: PepMab B.V., Lelystad (NL)

( * ) Notice: Subject to any disclaimer, the term of this patent is extended or adjusted under 35 U.S.C. 154(b) by 187 days.

This patent is subject to a terminal disclaimer.

(21) Appl. No.: 17/577,493

(22) Filed: Jan. 18, 2022

(65) Prior Publication Data

US 2022/0135693 A1    May 5, 2022

Related U.S. Application Data

(62) Division of application No. 16/813,780, filed on Mar. 10, 2020, now Pat. No. 11,254,749, which is a division of application No. 15/751,169, filed as application No. PCT/EP2016/069055 on Aug. 10, 2016, now Pat. No. 10,640,565.

(30) Foreign Application Priority Data

Aug. 10, 2015   (EP) .................... 15180415

(51) Int. Cl.
*C07K 16/28*      (2006.01)
*A61K 39/395*    (2006.01)

(52) U.S. Cl.
CPC .... *C07K 16/2866* (2013.01); *A61K 39/39558* (2013.01); *C07K 2317/24* (2013.01); *C07K 2317/34* (2013.01); *C07K 2317/565* (2013.01); *C07K 2317/567* (2013.01); *C07K 2317/734* (2013.01); *C07K 2317/76* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | | | |
|---|---|---|---|---|
| 5,595,756 | A * | 1/1997 | Bally | A61K 9/1272 264/4.1 |
| 10,640,565 | B2 * | 5/2020 | Back | A61P 17/06 |
| 11,254,749 | B2 * | 2/2022 | Back | A61P 29/00 |

FOREIGN PATENT DOCUMENTS

| WO | WO2007/003426 A1 | 1/2007 |
|---|---|---|
| WO | WO2009/139853 A2 | 11/2009 |
| WO | WO2012/043533 A1 | 5/2012 |
| WO | WO2014/151834 A2 | 9/2014 |
| WO | WO2013/184200 A1 | 12/2014 |

OTHER PUBLICATIONS

Wynn et al (Nat Med. ; 18(7): 1028-1040; Jan. 2013) (Year: 2013).*
Ma (Modern Drug Discovery 2004, 7(6)) (Year: 2004).*
Nanchahal et al (Proc Natl Acad Sci U S A. Jul. 5, 2016;113(27):7291-3) (Year: 2016).*
Steinman et al (Nat Med. Jan. 6, 2012;18(1):59-65) (Year: 2012).*
Blumberg et al (Nat Med.; 18(1): 35-41) (Year: 2015).*
Sporn et al, "Chemoprevention of Cancer," Carcinogenesis, vol. 21 (2000), 525-530 (Year: 2000).*
Auerbach et al (Cancer and Metastasis Reviews, 2000, 19: 167-172) (Year: 2000).*
Gura T (Science, 1997, 278(5340): 1041-1042 (Year: 1997).*
Jain RK (Scientific American, Jul. 1994,58-65) (Year: 1994).*
Kitko (Biol Blood Marrow Transplant. Jan. 2012 ; 18(1 Suppl): S46-S52) (Year: 2012).*
Wada et al (Kidney International, vol. 72, Issue 3, Aug. 1, 2007, pp. 269-273) (Year: 2007).*
Habiel et al (Front Pharmacol. Jan. 23, 2014:5:2) (Year: 2014).*
Pierce et al (The American Journal of Pathology, vol. 170, Issue 4, Apr. 2007, pp. 1152-1164) (Year: 2007).*
Birkenbach M, Josefsen K, Yalamanchili R, Lenoir G, Kieff E. Epstein-Barr virus-induced genes: first lymphocyte-specific G protein-coupled peptide receptors. Journal of Virology. 1993;67(4):2209-2220.
Luchtefeld, Maren, Christina Grothusen, Andreas Gagalick, Kumaravelu Jagavelu, Harald Schuett, Uwe JF Tietge, Oliver Pabst et al. "Chemokine Receptor 7 Knockout Attenuates Atherosclerotic Plaque DevelopmentClinical Perspective." Circulation 122, No. 16 (2010): 1621-1628.
Evans, Vanessa A., Gabriela Khoury, Suha Saleh, Paul U. Cameron, and Sharon R. Lewin. "HIV persistence: chemokines and their signalling pathways." Cytokine & growth factor reviews 23, No. 4-5 (2012): 151-157.
Ben-Baruch, Adit. "Site-specific metastasis formation: chemokines as regulators of tumor cell adhesion, motility and invasion." Cell adhesion & migration 3, No. 4 (2009): 328-333.
Viola, Antonella, and Andrew D. Luster. "Chemokines and their receptors: drug targets in immunity and inflammation." Annu. Rev. Pharmacol. Toxicol. 48 (2008): 171-197.
Steinman, Lawrence, et al. "Optimization of current and future therapy for autoimmune diseases." Nature medicine 18.1 (2012}: 59-65.

(Continued)

*Primary Examiner* — Brian Gangle
*Assistant Examiner* — Andrea K McCollum
(74) *Attorney, Agent, or Firm* — N.V. Nederlandsch Octrooibureau

(57) ABSTRACT

The present invention provides novel humanized anti-human C-C chemokine receptor type 7 (CCR7) antibodies and compositions comprising such antibodies. The antibodies and compositions are useful in the treatment of a cancer of which the tumour cells express a CCR7 receptor, in the treatment of inflammatory conditions, conditions or complications arising from tissue or organ transplantations, and conditions or complications arising from or associated with fibrosis. The invention further provides nucleic acid molecules encoding the anti-CCR7 antibodies, cells expressing the anti-CCR7 antibodies and methods for producing the anti-CCR7 antibodies.

9 Claims, 6 Drawing Sheets

Specification includes a Sequence Listing.

(56) References Cited

OTHER PUBLICATIONS

Sporn, Michael B., and Nanjoo Suh. "Chemoprevention of cancer." Carcinogenesis 21.3 (2000): 525-530.
Nanchahal, Jagdeep, and Boris Hinz. "Strategies to overcome the hurdles to treat fibrosis, a major unmet clinical need." Proceedings of the National Academy of Sciences 113.27 (2016): 7291-7293.
Ma, Chaoyong. "Animal models of disease In vivo assays are not usually performed until or after lead optimization is complete." Modern drug discovery 7 (2004): 30-36.
Jain, Rakesh K. "Barriers to drug delivery in solid tumors." Scientific American 271.1 (1994): 58-65.
Gura, Trisha. "Systems for identifying new drugs are often faulty." (1997): 1041-1042.
Brown, McKay, et al. "Tolerance of single, but not multiple, amino acid replacements in antibody VH CDR 2: a means of minimizing B cell wastage from somatic hypermutation?." The Journal of Immunology 156.9 (1996): 3285-3291.
Blumberg, Richard S., et al. "Unraveling the autoimmune translational research process layer by layer." Nature medicine 18.1 (2012): 35-41.
Auerbach, Robert, et al. "Angiogenesis assays: problems and pitfalls." Cancer and Metastasis Reviews 19.1-2 (2000): 167-172.
Vajdos, Felix F., et al. "Comprehensive functional maps of the antigen-binding site of an anti-ErbB2 antibody obtained with shotgun scanning mutagenesis." Journal of molecular biology 320.2 (2002): 415-428.
Cuesta-Mateos, Carlos, et al. "Evaluation of therapeutic targeting of CCR7 in acute graft-versus-host disease." Bone marrow transplantation 55.10 (2020): 1935-1945.
Ensminger, Stephan M., et al. "Increased transplant arteriosclerosis in the absence of CCR7 is associated with reduced expression of Foxp3." Transplantation 86.4 (2008): 590-600.
Gregson, Aric L., et al. "Protection against bronchiolitis obliterans syndrome is associated with allograft CCR7+ CD45RA-T regulatory cells." PLoS One 5.6 (2010): e11354.
Merck Manual—Overview of Transplantation By Martin Hertl. MD, PhD, Rush University Medical Center Lastfull review/revision Jun. 2020 \ Content last modified Jun. 2020.
Yan, Yan, et al. "CCL19 and CCR7 expression, signaling pathways, and adjuvant functions in viral infection and prevention." Frontiers in cell and developmental biology 7 (2019): 212.

* cited by examiner

HUMANIZED ANTI-CCR7 RECEPTOR ANTIBODIES

FIELD OF THE INVENTION

The present invention relates in general to the fields of medicine and pharmacy, in particular to the field of biopharmaceuticals for use in oncology. More specifically, the invention relates to anti-CCR7 receptor antibodies that are useful in the treatment of cancers wherein the tumour cells express a CCR7 receptor.

BACKGROUND OF THE INVENTION

Human CC motif receptor 7 (hereinafter referred to as "CCR7") is a seven transmembrane-spanning domain G-protein coupled receptor (GPCR) that was originally found to be expressed in a lymphocyte-selective manner by EBV infection (Birkenbach et al., 1993, J. Virol. 67: 2209-2220). Later CCR7 was found to be a selective chemokine receptor for CCL19 and CCL21. Under physiological conditions, expression of CCR7 is restricted to naïve T and B lymphocytes and mature dendritic cells and plays a roles in regulating their migration, organization, and activation.

CCR7 activity has been implicated in a diverse variety of disease states, including chronic inflammatory conditions (Moschovakis et al., 2012, Eur J Immunol. 42:1949-55), atherosclerosis (Luchtefeld et al., 2010, Circulation 122: 1621-28), HIV infection (Evans et al., 2012, Cytokine Growth Factor Rev. 23:151-57) and cancer (Ben-Baruch, 2009, Cell Adhesion Migration 3:328-33).

Various studies have revealed that CCR7 is expressed in a wide variety of tumour cells, including e.g. mantle cells lymphoma (MCL), follicular lymphoma, large B-cell lymphoma, AIDS-associated lymphoma, lymphoplasmacytic lymphoma, Burkitt lymphoma, B-cell acute lymphoblastic leukaemia, Hodgkin's disease, adult T-cell leukaemia/lymphoma, mycosis fungoides, blast crisis of chronic myeloproliferative syndromes, blast crisis of myelodysplastic syndromes, cancers such as breast cancer, non-small cell lung cancer, melanoma, gastric cancer or squamous cell carcinoma of the head and neck and colon carcinoma as B cell chronic lymphocytic leukemia, non-Hodgkin's lymphoma, breast cancer cell and malignant mammary tumor (WO 2007/003426). Further it is becoming clear that CCR7 plays a role in lymph node metastasis of various cancers (Viola and Luster, 2008, Annu Rev Pharmacol Toxicol. 48:171-97).

A reference mouse monoclonal antibody against human CCR7 (MAB197, Clone #150503) is commercially available from R&D Systems (www.RnDSystems.com).

WO 2007/003426 discloses the use of an antibody which binds to a CCR7 for treating cancer, whereby the tumor cells express CCR7. Binding of the antibody to the CCR7 expressing tumor cells is disclosed to inhibit migration of tumor cells and/or to kills tumor cells by one or more of complement-dependent cytotoxicity (CDC), antibody-dependent cell-mediated cytotoxicity (ADCC) and inducing apoptosis.

WO 2012/043533 discloses 8 different mouse monoclonal antibodies against human CCR7 that are useful for treating fibrosis or cancer. However, none of these antibodies has an IC50 of less than 7.4 nM for inhibiting intracellular $Ca^{2+}$ signal transduction.

WO 2014/151834 discloses three different human anti-CCR7 antibodies generated in a Xenomous™ immunized with human CCR7-expressing cells, as well as a mouse anti-human CCR7 antibody and chimerization and humanization thereof. The human anti-CCR7 antibodies bind to different epitope on human CCR7 than the reference mouse monoclonal antibody MAB197. The antibodies are disclosed to be useful for treating inflammatory conditions, cancerous conditions, as well as conditions and complications arising from tissue or organ transplantation. WO 2014/151834 further discloses the isolation of mouse anti-human CCR7 antibodies, among which the blocking antibody MAb 22, which was chimerized by replacing its heavy chain constant regions with their human counterparts. This chimerized antibody retained its ability to bind human CCR7. The light chain of this chimerized antibody was further altered to generate a series MAb 22 variants with chimerized heavy chains and humanized light chains. WO 2014/151834 does not disclose which, if any, of these MAb 22 variants with humanized light chains has retained the ability to bind human CCR7.

There is however still a need in the art for further and improved anti-CCR7 antibodies that are useful in human therapy.

SUMMARY OF THE INVENTION

In a first aspect the invention pertains to a humanized anti-CCR7 antibody comprising the hypervariable regions HVR-H1, HVR-H2, HVR-H3, HVR-L1, HVR-L2 and HVR-L3, wherein: HVR-H1 comprises the sequence: G-F/L-T/A/P-F-S/T/R-N/D/S-Y/F-A; HVR-H2 H1 comprises the sequence: I-S-S/D-G/R-G-S/T/F-Y/H/F-T/P; HVR-H3 H1 comprises the sequence: A/T/V/G-R-R/A-A/E/T-Y/G/T-R/V-Y/V-D/*-GTG/*-E/V/D/A/G/*-N/S/D/T-A/S/D-M/L/F-Y/S; HVR-L1 H1 comprises the sequence: Q/S-D/S-I/L/V-G/S/L-D/S/P/G/N-S/N-*/Y/DGKTY; HVR-L2 H1 comprises the sequence: A/S/T-T/I/V-S; and HVR-L3 H1 comprises the sequence: L/W/Q-Q-Y/F/G/W-A/T/S-S/N/H-S/F/N-P-L/P/Q-T, wherein "*" indicates that no amino acid can be present in that position. The antibody of the invention preferably has at least one of a) a minimal affinity for the synthetic antigen SYM1899 with SEQ ID NO: 76 defined by a $K_d$ that is not more than a factor 10 higher than the $K_d$ of a mouse anti-CCR7 antibody of which the amino acid sequence of the heavy chain variable domain is SEQ ID NO: 1 and of which the amino acid sequence of the light chain variable domain is SEQ ID NO: 2; and, b) an $IC_{50}$ of no more than 100 nM for inhibiting at least one of CCR7-dependent intracellular signalling and CCR7 receptor internalization, by at least one CCR7-ligand selected from CCL19 and CCL21.

In a preferred embodiment, the antibody of the invention is a humanized anti-CCR7 antibody, wherein HVR-H1 comprises one of SEQ ID NO.'s 3-10; HVR-H2 comprises one of SEQ ID NO.'s 11-16; HVR-H3 comprises one of SEQ ID NO.'s 17-23; HVR-L1 comprises one of SEQ ID NO.'s 24-30; HVR-L2 comprises one of SEQ ID NO.'s 31-33; and HVR-L3 comprises one of SEQ ID NO.'s 34-39. More preferably the humanized anti-CCR7 antibody of the invention comprises HVR-H1, HVR-H2, HVR-H3, HVR-L1, HVR-L2 and HVR-L3, wherein each, in order, comprises: (i) SEQ ID NO.'s 3, 11, 17, 24, 32, and 34; (ii) SEQ ID NO.'s 4, 12, 18, 25 31, and 35; (iii) SEQ ID NO.'s 5, 12, 18, 26, 31, and 35; (iv) SEQ ID NO.'s 6, 13, 19, 27, 31, and 36; (v) SEQ ID NO.'s 7, 14, 20, 24, 31, and 35; (vi) SEQ ID NO.'s 8, 15, 21, 28, 31 and 37; (vii) SEQ ID NO.'s 9, 16, 22, 29, 33 and 38; or (viii) SEQ ID NO.'s 10, 14, 23, 30, 31 and 39.

In a further preferred embodiment, the antibody of the invention is a humanized anti-CCR7 antibody, wherein the heavy chain variable domain of the antibody comprises 4 heavy chain framework regions, HFR1 to HFR4, and 3 hypervariable regions HVR-H1 to HVR-H3 that are operably linked in the order HFR1, HVR-H1, HFR2, HVR-H2, HFR3, HVR-H3 and HFR4, wherein the light chain variable domain of the antibody comprises 4 light chain framework regions, LFR1 to LFR4, and 3 hypervariable regions HVR-L1 to HVR-L3 that are operably linked in the order LFR1, HVR-L1, LFR2, HVR-L2, LFR3, HVR-L3 and LFR4, wherein the heavy chain framework regions HFR1 to HFR4 have the amino acid sequences of: i) SEQ ID NO's: 40, 43, 45 and 48, respectively (=FRs from VH1); ii) SEQ ID NO's: 41, 44, 46 and 49, respectively (=FRs from VH2); or, iii) SEQ ID NO's: 42, 44, 47 and 49, respectively (=FRs from VH3), and wherein the light chain framework regions LFR1 to LFR4 have the amino acid sequences of: iv) SEQ ID NO's: 50, 52, 55 and 58, respectively (=FRs from VL1); or, v) SEQ ID NO's: 51, 53, 56 and 59, respectively (=FRs from VL2).

In again a further preferred embodiment, the antibody of the invention is a humanized anti-CCR7 antibody, wherein the heavy chain variable domain of the antibody comprises an amino acid sequence with at least 95% sequence identity to at least one of SEQ ID NO's: 61, 62 and 63 (VH1, 2 or 3), and wherein the light chain variable domain of the antibody comprises an amino acid sequence with at least 95% sequence identity to at least one of SEQ ID NO's: 64 and 65 (VK1 or 2), wherein preferably the heavy chain variable domain of the antibody comprises the amino acid sequence of SEQ ID NO: 61 and preferably the light chain variable domain of the antibody comprises the amino acid sequence of SEQ ID NO: 64.

A humanized anti-CCR7 antibody according to any of the above embodiments of the invention, preferably comprises a heavy chain constant region that is IgG1, IgG2, IgG3 or IgG4 region.

A humanized anti-CCR7 antibody according to any of the above embodiments of the invention, preferably comprises a functional Fc region possessing at least one effector function selected from the group consisting of: C1q binding, complement dependent cytotoxicity; Fc receptor binding, antibody-dependent cell-mediated cytotoxicity and phagocytosis.

In a second aspect, the invention relates to a pharmaceutical composition comprising a humanized anti-CCR7 antibody according to any of the above embodiments of the invention.

In a third aspect, the invention relates to: a) a humanized anti-CCR7 antibody according to any one of the above embodiments of the invention; or b) a pharmaceutical composition comprising such antibody; for use as a medicament.

In a fourth aspect, the invention relates to a) a humanized anti-CCR7 antibody according to any one of the above embodiments of the invention; or b) a pharmaceutical composition comprising such antibody; for use in the treatment of a cancer, an inflammatory condition, a condition or complication arising from tissue or organ transplantation, or a condition or complication arising from or associated with fibrosis. Preferably, in the treatment, the cancer is a cancer of which the tumour cells express a CCR7 receptor, preferably the cancer is selected from the group consisting of chronic lymphocytic leukaemia (CLL), mantle cells lymphoma (MCL), follicular lymphoma, large B-cell lymphoma, AIDS-associated lymphoma, lymphoplasmacytic lymphoma, Burkitt lymphoma, B-cell acute lymphoblastic leukaemia, Hodgkin's disease, adult T-cell leukaemia/lymphoma, mycosis fungoides, blast crisis of chronic myeloproliferative syndromes, blast crisis of myelodysplastic syndromes, breast cancer, non-small cell lung cancer, melanoma, gastric cancer, squamous cell carcinoma of the head and neck and colon carcinoma. Preferably, in the treatment, the inflammatory condition is selected from the group consisting of in inflammatory bowel disease, Crohn's disease, ulcerative colitis, asthma, allergic airway inflammation, airway smooth muscle hyperplasia, fibrotic lung diseases, rheumatoid arthritis, multiple sclerosis, psoriasis, atherosclerosis, HIV infection and AIDS, or wherein the tissue or organ transplantation is one or more of kidney, heart, skin, and lung transplantation. Preferably, in the treatment, the fibrosis is selected from the group consisting of hepatic fibrosis and cirrhosis, renal fibrosis, pulmonary fibrosis, skin fibrosis, cardiovascular fibrosis, gastrointestinal fibrosis.

In a fifth aspect, the invention relates to a nucleic acid molecule comprising a nucleotide sequence encoding a humanized anti-CCR7 antibody according to any one of the above embodiments of the invention, wherein preferably the nucleic acid molecule comprises a nucleotide sequence encoding at least one of the heavy chain variable domain and the light chain variable domain of the antibody, and wherein preferably the coding nucleotide sequence is operably linked to regulatory sequences for expression of the coding nucleotide sequence in a host cell.

In a sixth aspect, the invention relates to a host cell comprising a nucleic acid molecule according to the fifth aspect.

DESCRIPTION OF THE INVENTION

Definitions

The term "antibody" is used in the broadest sense and specifically covers, e.g. single anti-CCR7 monoclonal antibodies, including antagonist, neutralizing antibodies, full length or intact monoclonal antibodies, anti-CCR7 antibody compositions with polyepitopic specificity, polyclonal antibodies, multivalent antibodies, single chain anti-CCR7 antibodies and fragments of anti-CCR7 antibodies (see below), including Fab, Fab', F(ab')2 and Fv fragments, diabodies, single domain antibodies (sdAbs), as long as they exhibit the desired biological and/or immunological activity. The term "immunoglobulin" (Ig) is used interchangeable with antibody herein. An antibody can be human and/or humanized.

The term "anti-CCR7 antibody" or "an antibody that binds to CCR7" refers to an antibody that is capable of binding CCR7 with sufficient affinity such that the antibody is useful as a diagnostic and/or therapeutic agent in targeting CCR7. Preferably, the extent of binding of an anti-CCR7 antibody to an unrelated, non-CCR7 protein is less than about 10% of the binding of the antibody to CCR7 as measured, e.g., by a radioimmunoassay (RIA) or ELISA. In certain embodiments, an antibody that binds to CCR7 has a dissociation constant (Kd) of ≤1 mM, ≤100 nM, ≤10 nM, ≤1 nM, or ≤0.1 nM. In certain embodiments, anti-CCR7 antibody binds to an epitope of CCR7 that is conserved among CCR7 from different species.

An "isolated antibody" is one which has been identified and separated and/or recovered from a component of its natural environment. Contaminant components of its natural environment are materials which would interfere with therapeutic uses for the antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least residues of N-terminal or internal amino acid sequence by use of a spinning cup sequenator, or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 Daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, CT, 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated α, δ, ε, γ, and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The "variable region" or "variable domain" of an antibody refers to the amino-terminal domains of the heavy or light chain of the antibody. The variable domain of the heavy chain may be referred to as "$V_H$." The variable domain of the light chain may be referred to as "$V_L$." These domains are generally the most variable parts of an antibody and contain the antigen-binding sites.

The term "variable" refers to the fact that certain segments of the variable domains differ extensively in sequence among antibodies. The V domain mediates antigen binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" (HVRs) that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, MD (1991)). The constant domains are not involved directly in binding an antibody to an antigen, but exhibit various effector functions, such as participation of the antibody in antibody dependent cellular cytotoxicity (ADCC).

An "intact" antibody is one which comprises an antigen-binding site as well as a CL and at least heavy chain constant domains, $C_H1$, $C_H2$ and $C_H3$. The constant domains may be native sequence constant domains (e.g. human native sequence constant domains) or amino acid sequence variant thereof. Preferably, the intact antibody has one or more effector functions.

A "naked antibody" for the purposes herein is an antibody that is not conjugated to a cytotoxic moiety or radiolabel.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870, Example 2; Zapata et al., Protein Eng. 8(10): 1057-1062 [1995]); single-chain antibody molecules; and multispecific antibodies formed from antibody fragments. In one embodiment, an antibody fragment comprises an antigen binding site of the intact antibody and thus retains the ability to bind antigen.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')2 fragment which roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments, which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). Chimeric antibodies of interest herein include "primatized" antibodies comprising variable domain antigen-binding sequences derived from a non-human primate (e.g. Old World Monkey, Ape etc.), and human constant region sequences.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, a few framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992). See also the following review articles and references cited therein: Vaswani and Hamilton, Ann. Allergy, Asthma and Immunol., 1:105-115 (1998); Harris, Biochem. Soc. Transactions, 23:1035-1038 (1995); Hurle and Gross, Curr. Op. Biotech., 5:428-433 (1994).

The term "hypervariable region", "HVR", when used herein refers to the regions of an antibody variable domain which are hypervariable in sequence and/or form structurally defined loops that are responsible for antigen binding. Generally, antibodies comprise six hypervariable regions; three in the VH (H1, H2, H3), and three in the VL (L1, L2, L3). A number of hypervariable region delineations are in use and are encompassed herein. The hypervariable regions generally comprise amino acid residues from a "complementarity determining region" or "CDR" (e.g., around about residues 24-34 (L1), 50-56 (L2) and 89-97 (L3) in the VL, and around about 31-35 (H1), 50-65 (H2) and 95-102 (H3) in the VH when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (L1), 50-56 (L2) and 89-97 (L3) in the VL, and 26-32 (H1), 52-56 (H2) and 95-101 (H3) in the VH when numbered in accordance with the Chothia numbering system; Chothia and Lesk, J. Mol. Biol. 196:901-917 (1987)); and/or those residues from a "hypervariable loop"/CDR (e.g., residues 27-38 (L1), 56-65 (L2) and 105-120 (L3) in the VL, and 27-38 (H1), 56-65 (H2) and 105-120 (H3) in the VH when numbered in accordance with the IMGT numbering system; Lefranc, M. P. et al. Nucl. Acids Res. 27:209-212 (1999), Ruiz, M. et al. Nucl. Acids Res. 28:219-221 (2000)). Optionally the antibody has symmetrical insertions at one or more of the following points 28, 36 (L1), 63, 74-75 (L2) and 123 (L3) in the VL, and 28, 36 (H1), 63, 74-75 (H2) and 123 (H3) in the VH when numbered in accordance with Honneger, A. and Plunkthun, A. J. (Mol. Biol. 309:657-670 (2001)). The hypervariable regions/CDRs of the antibodies of the invention are preferably defined and numbered in accordance with the IMGT numbering system.

"Framework" or "FR" residues are those variable domain residues other than the hypervariable region residues herein defined.

A "blocking" antibody or an "antagonist" antibody is one which inhibits or reduces biological activity of the antigen it binds. Preferred blocking antibodies or antagonist antibodies substantially or completely inhibit the biological activity of the antigen.

An "agonist antibody", as used herein, is an antibody which mimics at least one of the functional activities of a polypeptide of interest.

A "species-dependent antibody," e.g., a mammalian anti-human IgE antibody, is an antibody which has a stronger binding affinity for an antigen from a first mammalian species than it has for a homologue of that antigen from a second mammalian species. Normally, the species-dependent antibody "bind specifically" to a human antigen (i.e., has a binding affinity (Kd) value of no more than about $1\times10^{-7}$ M, preferably no more than about $1\times10^{-8}$ M and most preferably no more than about $1\times10^{-9}$ M) but has a binding affinity for a homologue of the antigen from a second non-human mammalian species which is at least about 50 fold, or at least about 500 fold, or at least about 1000 fold, weaker than its binding affinity for the human antigen. The species-dependent antibody can be of any of the various types of antibodies as defined above, but preferably is a humanized or human antibody.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_d$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

A "$K_d$" or "$K_d$ value" can be measured by using surface plasmon resonance assays using a BIAcore™-2000 or a BIAcore™-3000 (BIAcore, Inc., Piscataway, NJ) at 25° C. with immobilized antigen CM5 chips at ~10-50 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 μg/ml (~0.2 μM) before injection at a flow rate of 5 μl/minute to achieve approximately 10 response units (RU) of coupled protein.

Following the injection of antigen, 1M ethanolamine is injected to block unreacted groups. For kinetics measurements, two-fold serial dilutions of the antibody or Fab (0.78 nM to 500 nM) are injected in PBS with 0.05% TWEEN 20 (polysorbate 20) (PBST) at 25° C. at a flow rate of approximately 25 μl/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant ($K_d$) is calculated as the ratio $k_{off}/k_{on}$. See, e.g., Chen, Y., et al., (1999) J. Mol Biol 293:865-881. If the on-rate exceeds $10^6$ $M^{-1}$ $S^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stir red cuvette.

An "on-rate" or "rate of association" or "association rate" or "$k_{on}$" according to this invention can also be determined with the same surface plasmon resonance technique described above using a BIAcore™-2000 or a BIAcore™-3000 (BIAcore, Inc., Piscataway, NJ) as described above.

An antibody "which binds" an antigen of interest, e.g. a tumor-associated polypeptide CCR7 antigen target, is one that binds the antigen with sufficient affinity such that the antibody is useful as a therapeutic agent in targeting a cell or tissue expressing the antigen, and does not significantly cross-react with other proteins. In such embodiments, the extent of binding of the antibody to a "non-target" protein will be less than about 10% of the binding of the antibody to its particular target protein as determined by fluorescence activated cell sorting (FACS) analysis or radioimmunoprecipitation (RIA). With regard to the binding of an antibody to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labelled target. In this case, specific binding is indicated if the binding of the labelled target to a probe is competitively inhibited by excess unlabelled target. The term "specific binding" or "specifically binds to" or is "specific for" a particular polypeptide or an epitope on a particular polypeptide target as used herein can be exhibited, for example, by a molecule having a $K_d$ for the target (which may be determined as described above) of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. In one embodiment, the term "specific binding" refers to binding where a molecule binds to a particular polypeptide or epitope on a particular polypeptide without substantially binding to any other polypeptide or polypeptide epitope.

The term "epitope" is the portion of a molecule that is bound by an antigen binding protein, e.g. an antibody. The term includes any determinant capable of specifically binding to an antigen binding protein, such as an antibody or to a T-cell receptor. An epitope can be contiguous or non-contiguous (e.g., in a polypeptide, amino acid residues that are not contiguous to one another in the polypeptide sequence but that within in context of the molecule are bound by the antigen binding protein). In certain embodiments, epitopes may be mimetic in that they comprise a three dimensional structure that is similar to an epitope used to generate the antigen binding protein, yet comprise none or only some of the amino acid residues found in that epitope used to generate the antigen binding protein. Most often, epitopes reside on proteins, but in some instances may reside on other kinds of molecules, such as nucleic acids. Epitope determinants may include chemically active surface groupings of molecules such as amino acids, sugar side chains, phosphoryl, sulfonyl or sulfate groups, and may have specific three dimensional structural characteristics, and/or specific charge characteristics. Generally, antibodies specific for a particular target antigen will preferentially recognize an epitope on the target antigen in a complex mixture of proteins and/or macromolecules.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

A "functional Fc region" possesses an "effector function" of a native sequence Fc region. Exemplary "effector functions" include C1q binding; CDC; Fc receptor binding; ADCC; phagocytosis; down regulation of cell surface receptors (e.g. B cell receptor; BCR), etc. Such effector functions generally require the Fc region to be combined with a binding domain (e.g. an antibody variable domain) and can be assessed using various assays as disclosed, for example, in definitions herein.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol. 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. (USA) 95:652-656 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M. in Daëron, Annu. Rev. Immunol. 15:203-234 (1997)). FcRs are reviewed in Ravetch and Kinet, Annu. Rev. Immunol. 9:457-492 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)).

Binding to human FcRn in vivo and serum half-life of human FcRn high affinity binding polypeptides can be assayed, e.g., in transgenic mice or transfected human cell lines expressing human FcRn, or in primates to which the polypeptides with a variant Fc region are administered. WO 2000/42072 (Presta) describes antibody variants with improved or diminished binding to FcRs. See also, e.g., Shields et al. J. Biol. Chem. 9(2):6591-6604 (2001).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., J. Immunol. Methods 202:163 (1996), may be performed. Antibody variants with altered Fc region amino acid sequences (antibodies with a variant Fc region) and increased or decreased C1q binding capability are described, e.g., in U.S. Pat. No. 6,194,551 B1 and WO 1999/51642. See also, e.g., Idusogie et al., J. Immunol. 164: 4178-4184 (2000). One such substitution that increases C1q binding, and thereby an increases CDC activity, is the E333A substitution, which can advantageously be applied in the antibodies of the invention.

The term "Fc region-comprising antibody" refers to an antibody that comprises an Fc region. The C-terminal lysine (residue 447 according to the EU numbering system) of the Fc region may be removed, for example, during purification of the antibody or by recombinant engineering of the nucleic acid encoding the antibody. Accordingly, a composition comprising an antibody having an Fc region according to this invention can comprise an antibody with K447, with all K447 removed, or a mixture of antibodies with and without the K447 residue.

"Sequence identity" and "sequence similarity" can be determined by alignment of two amino acid sequences or two nucleotide sequences using global or local alignment algorithms, depending on the length of the two sequences. Sequences of similar lengths are preferably aligned using a global alignment algorithms (e.g. Needleman and Wunsch) which aligns the sequences optimally over the entire length, while sequences of substantially different lengths are preferably aligned using a local alignment algorithm (e.g. Smith Waterman). Sequences may then be referred to as "substantially identical" or "essentially similar" when they (when optimally aligned by for example the programs GAP or BESTFIT using default parameters) share at least a certain minimal percentage of sequence identity (as defined below). GAP uses the Needleman and Wunsch global alignment algorithm to align two sequences over their entire length (full length), maximizing the number of matches and minimizing the number of gaps. A global alignment is suitably used to determine sequence identity when the two sequences have similar lengths. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, CA 92121-3752 USA, or using open source software, such as the program "needle" (using the global Needleman Wunsch algorithm) or "water" (using the local Smith Waterman algorithm) in EmbossWIN version 2.10.0, using the same parameters as for GAP above, or using the default settings (both for 'needle' and for 'water' and both for protein and for DNA alignments, the default Gap opening penalty is 10.0 and the default gap extension penalty is 0.5; default scoring matrices are Blossum62 for proteins and DNAFull for DNA). When sequences have a substantially different overall lengths, local alignments, such as those using the Smith Waterman algorithm, are preferred. Alternatively percentage similarity or identity may be determined by searching against public databases, using algorithms such as FASTA, BLAST, etc.

Once two amino acid sequences are aligned using any of the above alignment programs, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

A "nucleic acid construct" or "nucleic acid vector" is herein understood to mean a man-made nucleic acid molecule resulting from the use of recombinant DNA technology. The term "nucleic acid construct" therefore does not include naturally occurring nucleic acid molecules although a nucleic acid construct may comprise (parts of) naturally occurring nucleic acid molecules. The terms "expression vector" or "expression construct" refer to nucleotide sequences that are capable of effecting expression of a gene in host cells or host organisms compatible with such sequences. These expression vectors typically include at least suitable transcription regulatory sequences and optionally, 3' transcription termination signals. Additional factors necessary or helpful in effecting expression may also be present, such as expression enhancer elements. The expression vector will be introduced into a suitable host cell and be able to effect expression of the coding sequence in an in vitro cell culture of the host cell. The expression vector will be suitable for replication in the host cell or organism of the invention.

As used herein, the term "promoter" or "transcription regulatory sequence" refers to a nucleic acid fragment that functions to control the transcription of one or more coding sequences, and is located upstream with respect to the direction of transcription of the transcription initiation site of the coding sequence, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active in most tissues under most physiological and developmental conditions. An "inducible" promoter is a promoter that is physiologically or developmentally regulated, e.g. by the application of a chemical inducer.

As used herein, the term "operably linked" refers to a linkage of polynucleotide elements in a functional relationship. A nucleic acid is "operably linked" when it is placed into a functional relationship with another nucleic acid sequence. For instance, a transcription regulatory sequence is operably linked to a coding sequence if it affects the transcription of the coding sequence. Operably linked means that the DNA sequences being linked are typically contiguous and, where necessary to join two protein encoding regions, contiguous and in reading frame.

DETAILED DESCRIPTION OF THE INVENTION

Anti-CCR7 Antibodies of the Invention

In a first aspect, the invention provides antigen binding proteins that bind to CCR7. An antigen binding protein of the invention that binds to CCR7 preferably is an anti-CCR7 antibody in the broadest sense as defined herein above, including e.g. anti-CCR7 antibodies, antibody fragments, antibody derivatives, antibody muteins, and antibody variants. An anti-CCR7 antibody of the invention preferably is an isolated is antibody. Preferably, an anti-CCR7 antibody of the invention binds to a primate CCR7, more preferably to human CCR7. An amino acid sequence of human CCR7 is available in GenBank: EAW60669.1 (SEQ ID NO: 75). Amino acids 1 to 24 of this sequence comprise the membrane translocation signal peptide, which is cleaved off during expression. Amino acids 25 to 59 of human CCR7 make up the N-terminal extracellular domain, which domain comprises sulfated tyrosine residues in position $Y_{32}$ and $Y_{41}$. Various allelic variants are known for human CCR7 with one or more amino acid substitutions compared to the sequence in GenBank: EAW60669.1. "Human CCR7" in the present invention includes these allelic variants, at least in as far as the variants have an extracellular domain and the function of CCR7.

An anti-CCR7 antibody of the invention preferably specifically binds to the N-terminal extracellular domain of a CCR7, preferably a human CCR7. The antibody of the invention preferably specifically binds to an epitope comprising or consisting of the amino acid sequence "ZxLFE", wherein Z is a sulfated tyrosine and x can be any amino acid and F can be replaced by a hydrophobic amino acid. The antibody of the invention thus preferably specifically binds to an epitope comprising or consisting of the amino acids sequence "ZTLFE" in positions 41 to 45 in the N-terminal extracellular domain of human CCR7. The antibody preferably is specific for human CCR7.

An anti-CCR7 antibody of the invention preferably has a minimal affinity for human CCR7 or for a synthetic antigen comprising the "ZTLFE" epitope, preferably for the synthetic antigen SYM1899 as described in the Examples herein. Preferably therefore, the anti-CCR7 antibody of the invention has a $K_d$ of $1\times10^{-8}$ M, $5\times10^{-9}$ M, $2\times10^{-9}$ M, $1.8\times10^{-9}$ M, $1\times10^{-9}$ M, $1\times10^{-10}$ M or $1\times10^{-11}$ M or less. Alternatively, the minimal affinity of the antibody is defined by reference to the $K_d$ of a reference anti-CCR7 antibody when tested in the same assay. Thus, preferably an anti-CCR7 antibody of the invention has a $K_d$ for human CCR7 or for a synthetic antigen comprising the "ZTLFE" epitope (preferably the synthetic antigen SYM1899 as described in the Examples herein) that is not more than a factor 10, 5, 2, 1.5, 1.2, 1.1 or 1.05 higher than the $K_d$ of a reference anti-CCR7 antibody for the antigen, whereby the reference anti-CCR7 antibody is a mouse anti-CCR7 antibody of which the amino acid sequence of the heavy chain variable domain is SEQ ID NO: 1 and of which the amino acid sequence of the light chain variable domain is SEQ ID NO: 2. It is understood herein that an antibody with a $K_d$ that is not more than a factor 10 higher times than the $K_d$ of a reference is an antibody that has an affinity that is not less than a factor 10 lower than the affinity of the reference antibody. Thus if the reference antibody has a $K_d$ of $1\times10^{-9}$ M, the antibody in question has a $K_d$ of $1\times10^{-8}$ M or less.

An anti-CCR7 antibody of the invention preferably binds to human CCR7 or to a synthetic antigen comprising the "ZTLFE" epitope (preferably the synthetic antigen SYM1899 as described in the Examples herein; SEQ ID NO: 76) with a maximal $k_{off}$ rate constant. Preferably therefore, the anti-CCR7 antibody of the invention has a $k_{off}$ rate constant that is $1\times10^{-3}$, $1\times10^{-4}$ or $1\times10^{-5}$ s$^{-1}$ or less. Alternatively, the maximal $k_{off}$ rate constant of the antibody is defined by reference to the $k_{off}$ rate constant of a reference anti-CCR7 antibody when tested in the same assay. Thus, preferably an anti-CCR7 antibody of the invention binds to human CCR7 or to a synthetic antigen comprising the "ZTLFE" epitope (preferably the synthetic antigen SYM1899 as described in the Examples herein) that is not more than a factor 10, 5, 2, 1.5, 1.2, 1.1 or 1.05 higher than the $k_{off}$ rate constant of a reference anti-CCR7 antibody for the antigen, whereby the reference anti-CCR7 antibody is a mouse anti-CCR7 antibody of which the amino acid sequence of the heavy chain variable domain is SEQ ID NO: 1 and of which the amino acid sequence of the light chain variable domain is SEQ ID NO: 2.

An anti-CCR7 antibody of the invention preferably is a neutralizing antibody that inhibits CCR7-dependent intracellular signalling and/or CCR7 receptor internalization by at least one CCR7 ligand selected from CCL19 and CCL21. An anti-CCR7 antibody preferably has an IC$_{50}$ that is not higher than 150, 100, 80, 50, 30, 25, 20, 15, 10, 5 or 3 nM for inhibiting CCR7-dependent intracellular signalling and/or CCR7 receptor internalization by at least one CCR7 ligand selected from CCL19 and CCL21, as can e.g. be determined in assay as described in the Examples herein. Alternatively, the maximal IC$_{50}$ of the antibody is defined by reference to the IC$_{50}$ of a reference anti-CCR7 antibody when tested in the same assay. Thus, preferably an anti-CCR7 antibody of the invention has an IC$_{50}$ that is not more than a factor 10, 5, 2, 1.5, 1.2, 1.1 or 1.05 higher than the IC$_{50}$ of a reference anti-CCR7 antibody, whereby the reference anti-CCR7 antibody is a mouse anti-CCR7 antibody of which the amino acid sequence of the heavy chain variable domain is SEQ ID NO: 1 and of which the amino acid sequence of the light chain variable domain is SEQ ID NO: 2.

An anti-CCR7 antibody of the invention preferably inhibits CCR7-dependent intracellular signalling CCR7 as described above, without substantial agonistic effects, more preferably without detectable agonistic effects, as can e.g. be determined in assay as described in the Examples herein.

An anti-CCR7 antibody of the invention preferably comprises the hypervariable regions HVR-H1, HVR-H2, HVR-H3, HVR-L1, HVR-L2 and HVR-L3, wherein:
HVR-H1 comprises the sequence: G-F/L-T/A/P-F-S/T/R-N/D/S-Y/F-A;
HVR-H2 H1 comprises the sequence: I-S-S/D-G/R-G-S/T/F-Y/H/F-T/P;
HVR-H3 H1 comprises the sequence: A/T/V/G-R-R/A-A/E/T-Y/G/T-R/V-Y/V-D/*-GTG/*-E/V/D/A/G/*-N/S/D/T-A/S/D-M/L/F-Y/S;
HVR-L1 H1 comprises the sequence: Q/S-D/S-I/L/V-G/S/L-D/S/P/G/N-S/N-*/Y/DGKTY;
HVR-L2 H1 comprises the sequence: A/S/T-T/I/V-S; and
HVR-L3 H1 comprises the sequence: L/W/Q-Q-Y/F/G/W-A/T/S-S/N/H-S/F/N-P-L/P/Q-T, wherein "*" indicates that no amino acid can be present in that position.

More preferably, an anti-CCR7 antibody of the invention is an antibody wherein:
HVR-H1 comprises one of SEQ ID NO.'s 3-10; HVR-H2 comprises one of SEQ ID NO.'s 11-16; HVR-H3 comprises one of SEQ ID NO.'s 17-23; HVR-L1 comprises one of SEQ ID NO.'s 24-30; HVR-L2 comprises one of SEQ ID NO.'s 31-33; and HVR-L3 comprises one of SEQ ID NO.'s 34-39.

Most preferably, an anti-CCR7 antibody of the invention comprises HVR-H1, HVR-H2, HVR-H3, HVR-L1, HVR-L2 and HVR-L3, wherein each, in order, comprises: (i) SEQ ID NO.'s 3, 11, 17, 24, 32, and 34; (ii) SEQ ID NO.'s 4, 12, 18, 25 31, and 35; (iii) SEQ ID NO.'s 5, 12, 18, 26, 31, and 35; (iv) SEQ ID NO.'s 6, 13, 19, 27, 31, and 36; (v) SEQ ID NO.'s 7, 14, 20, 24, 31, and 35; (vi) SEQ ID NO.'s 8, 15, 21, 28, 31 and 37; (vii) SEQ ID NO.'s 9, 16, 22, 29, 33 and 38; or (viii) SEQ ID NO.'s 10, 14, 23, 30, 31 and 39.

An anti-CCR7 antibody of the invention can be a mouse antibody or a chimeric, e.g. mouse-human antibody. However preferably the antibody is a humanized antibody. A humanized antibody according to the invention preferably elicits little to no immunogenic response against the antibody in a subject to which the antibody is administered. For example, a humanized antibody according to the invention elicits and/or is expected to elicit a human anti-mouse antibody response (HAMA) at a substantially reduced level compared to the original mouse an antibody, e.g. comprising the sequence of SEQ ID NO: 1 and 2 in a host subject. Preferably, the humanized antibody elicits and/or is expected to elicit a minimal or no human anti-mouse antibody response (HAMA). Most preferably, an antibody of the invention elicits anti-mouse antibody response that is at or less than a clinically-acceptable level.

Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) Nature 321:522-525; Riechmann et al. (1988) Nature 332:323-327; Verhoeyen et al. (1988) Science 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody (Sims et al., 1993, J. Immunol. 151:2296; Chothia et al., 1987, J. Mol. Biol. 196:901). Another method uses a particular framework derived from the consensus sequence of all human antibodies of a particular subgroup of light or heavy chains. The same framework may be used for several different humanized antibodies (Carter et al. (1992) Proc. Natl. Acad. Sci. USA, 89:4285; Presta et al. (1993) J. Immunol, 151:2623).

It is further important that antibodies be humanized with retention of high affinity for the antigen and other favourable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

For the choice of the preferred human variable domain frame work regions, both light and heavy, used in making the preferred humanized antibodies of the invention, online databases of Human IgG sequences were searched for comparison to the murine VH domains of the 729 antibody using BLAST search algorithms. Candidate human variable domains were selected from the top 200 BLAST results. These were reduced to three candidates based on a combination of framework homology, maintaining key framework residues and canonical loop structure.

An anti-CCR7 antibody of the invention preferably is an antibody wherein the heavy chain variable domain of the antibody comprises 4 heavy chain framework regions, HFR1 to HFR4, and 3 hypervariable regions HVR-H1 to HVR-H3 that are operably linked in the order HFR1, HVR-H1, HFR2, HVR-H2, HFR3, HVR-H3 and HFR4, and wherein the light chain variable domain of the antibody comprises 4 light chain framework regions, LFR1 to LFR4, and 3 hypervariable regions HVR-L1 to HVR-L3 that are operably linked in the order LFR1, HVR-L1, LFR2, HVR-L2, LFR3, HVR-L3 and LFR4. Preferably, the heavy chain framework regions HFR1 to HFR4 in an antibody of the invention have the amino acid sequences of: i) SEQ ID NO's: 40, 43, 45 and 48, respectively (i.e. the FRs from VH1); ii) SEQ ID NO's: 41, 44, 46 and 49, respectively (i.e. the FRs from VH2); or, iii) SEQ ID NO's: 42, 44, 47 and 49, respectively (i.e. the FRs from VH3). Preferably, the light chain framework regions LFR1 to LFR4 in an antibody of the invention have the amino acid sequences of: iv) SEQ ID NO's: 50, 52, 55 and 58, respectively (i.e. the FRs from VL1); or, v) SEQ ID NO's: 51, 53, 56 and 59, respectively (i.e. the FRs from VL2).

Preferably in an anti-CCR7 antibody of the invention, wherein the heavy chain variable domain of the antibody comprises an amino acid sequence with at least 95, 96, 97, 98, 99 or 100% sequence identity to at least one of SEQ ID NO's: 61, 62 and 63 (VH1, 2 or 3), more preferably the heavy chain variable domain of the antibody comprises an amino acid sequence with at least 95, 96, 97, 98, 99 or 100% sequence identity to SEQ ID NO: 61.

Preferably in an anti-CCR7 antibody of the invention the light chain variable domain of the antibody comprises an amino acid sequence with at least 95, 96, 97, 98, 99 or 100% sequence identity to at least one of SEQ ID NO's: 64 and 65 (VK1 or 2), more preferably the light chain variable domain of the antibody comprises an amino acid sequence with at least 95, 96, 97, 98, 99 or 100% sequence identity to SEQ ID NO: 64.

A particularly preferred anti-CCR7 antibody of the invention comprises a heavy chain variable domain comprising the amino acid sequence of SEQ ID NO: 61 (i.e. the VH1 variable domain), and a light chain variable domain comprising the amino acid sequence of SEQ ID NO: 64 (i.e. the VK1 variable domain).

Amino acid sequence modification(s) of the anti-CCR7 antibody of the invention are contemplated. For example, it may be desirable to improve the binding affinity and/or other biological properties of the antibody. Amino acid sequence variants of the antibody are prepared by introducing appropriate nucleotide changes into the antibody encoding nucleic acid, or by peptide synthesis. Such modifications include, for example, deletions from, and/or insertions into and/or substitutions of, residues within the amino acid sequences of the antagonist. Any combination of deletion, insertion, and substitution is made to achieve the final construct, provided that the final construct possesses the desired characteristics. The amino acid changes may also alter post-translational processes of the antagonist, such as changing the number or position of glycosylation sites.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antagonist with an N-terminal methionyl residue or the antagonist fused to a cytotoxic polypeptide. Other insertional variants of the antagonist molecule include the fusion to the N- or C-terminus of the antagonist of an enzyme, or a polypeptide which increases the serum half-life of the antagonist.

Another type of variant is an amino acid substitution variant. These variants have at least one amino acid residue in the antagonist molecule replaced by a different residue. The sites of greatest interest for substitutional mutagenesis of antibody antagonists include the hypervariable regions, but FR alterations are also contemplated.

Another type of amino acid variant of the antibody alters the original glycosylation pattern of the antagonist. By altering is meant deleting one or more carbohydrate moieties found in the antagonist, and/or adding one or more glycosylation sites that are not present in the antagonist. Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of any of these tripeptide sequences in a polypeptide creates a potential glycosylation site. O-linked glycosylation refers to the attachment of one of the monosaccharides or monosaccharide derivatives N-acetylgalactosamine, galactose, or xylose to a hydroxyamino acid, most commonly serine or threonine, although 5-hydroxyproline or 5-hydroxylysine may also be used. Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites). Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antagonist.

In some embodiments, an anti-CCR7 antibody of the invention comprises a light chain and/or a heavy chain antibody constant region. Any antibody constant regions known in the art can be used. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. An anti-CCR7 antibody of the invention can thus have constant regions of any isotype, i.e. including IgG, IgM, IgA, IgD, and IgE constant regions as well as IgG1, IgG2, IgG3, or IgG4 constant regions. In one embodiment, the light or heavy chain constant region is a fragment, derivative, variant, or mutein of a naturally occurring constant region. Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype. See also Lantto et al. (2002, Methods Mol. Biol. 178:303-16). Accordingly, the anti-CCR7 antibodies of the invention include those comprising, for example, one or more of the variable domain sequences disclosed herein and having a desired isotype (e.g., IgA, IgG1, IgG2, IgG3, IgG4, IgM, IgE, and IgD), as well as Fab or F(ab')2 fragments thereof. Moreover, if an IgG4 is desired, it may also be desired to introduce a point mutation (CPSCP→CPPCP) in the hinge region as described in Bloom et al. (1997, Protein Science 6:407) to alleviate a tendency to form intra-H chain disulfide bonds that can lead to heterogeneity in the IgG4 antibodies.

An anti-CCR7 antibody of the invention preferably comprises a functional Fc region possessing at least one effector function selected from the group consisting of C1q binding, complement dependent cytotoxicity; Fc receptor binding, antibody-dependent cell-mediated cytotoxicity and phagocytosis.

An anti-CCR7 antibody of the invention can be modified to improve effector function, e.g. so as to enhance ADCC and/or CDC of the antibody. This can be achieved by introducing one or more amino acid substitutions in an Fc region of an antibody. A preferred substitution in the Fc region of an antibody of the invention is a substitution that increases C1q binding, and thereby an increases CDC activity, such as e.g. described in Idusogie et al., J. Immunol. 164: 4178-4184 (2000). A preferred substitution in the Fc region that increases C1q binding is the E333A substitution.

Glycosyl groups added to the amino acid backbone of glycoproteins e.g. antibodies are formed by several monosaccharides or monosaccharide derivatives in resulting in a composition which can be different in the same antibody produced in cell from different mammals or tissues. In addition, has been shown that different composition of glycosyl groups can affect the potency in mediating antigen-dependent cell-mediated cyotoxicity (ADCC) and/or complement dependent cytotoxicity (CDC) of the antibody. Therefore it is possible to improve those properties by mean of studying the pattern of glycosylation of antibodies from different sources. An example of such approach is Niwa et al. (2004, Cancer Res, 64(6):2127-33).

Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al. (1992, J. Exp Med. 176:1191-1195) and Shopes, (1992, Immunol. 148:2918-2922). Homodimeric antibodies with enhanced anti-tumour activity may also be prepared using heterobifunctional cross-linkers as described in Wolff et al. (1993, Cancer Research 53:2560-2565). Alternatively, an antibody which has dual Fc regions can be engineered and may thereby have enhanced complement lysis and ADCC capabilities. See Stevenson et al. (1989, Anti-Cancer Drug Design 3:2 19-230). In order to increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

A preferred anti-CCR7 antibody of the invention comprises a heavy chain constant region of the human allotype G1m17,1 (see Jefferis and Lefranc (2009) MAbs Vol. 1 Issue 4, pp 1-7), which heavy chain constant region comprises the amino acid sequence of SEQ ID NO.: 79. More preferably, the heavy chain constant region of the human allotype G1m17,1 in the antibody of the invention comprises an E333A substitution, which heavy chain constant region comprises the amino acid sequence of SEQ ID NO.: 80.

Cytotoxic chemotherapy or radiotherapy of cancer is limited by serious, sometimes life threatening, side effects that arise from toxicities to sensitive normal cells because the therapies are not selective for malignant cells. One strategy to avoid these problems is to couple the therapeutic agent to antibodies such the anti-CCR7 antibodies of the invention. This increases the exposure of the malignant cells, and reduces the exposure of normal cells, to the ligand-targeted therapeutics. See Allen, Nature, 2: 750-763 (2002). The therapeutic agent can be an immunosuppressive agent i.e. a substance that act to suppress or mask the immune system of the mammal being treated herein. This would include substances that suppress cytokine production, down-regulate or suppress self-antigen expression, or mask the MHC antigens. The therapeutic agent can also be a cytotoxic agent i.e. a substance that inhibits or prevents the function of cells and/or causes destruction of cells. The term is intended to include radioactive isotopes, chemotherapeutic agents i.e. chemical compounds useful in the treatment of cancer, and toxins such as small molecule toxins or enzymatically active toxins of bacterial, fungal, plant or animal origin, or fragments thereof. The therapeutic agent can also be a cytokine, an hormone, growth factor, necrosis factor i.e. a protein or peptide released by one cell population which act on another cell as intercellular mediators or even in the same cell population. As used herein, the term cytokine includes proteins and peptides from natural sources or from recombinant cell culture and biologically active equivalents of the native sequence cytokines. The therapeutic agent can also be a prodrug which refers to a precursor or derivative form of a pharmaceutically active substance that is less cytotoxic to tumour cells compared to the parent drug and is capable of being enzymatically activated or converted into the more active parent form. Conjugates of an antibody and one or more small molecule toxins.

In one preferred embodiment of the invention, anti-CCR7 antibody of the invention is conjugated to one or more toxin molecules. Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha sarcin, *Aleurites fordii* proteins, dianthin proteins, *Phytolaca americana* proteins (PAP1, PAP11, and PAP-S), *Momordica charantia* inhibitor, curcin, crotin, *Sapaonaria officinalis* inhibitor, gelonin, mitogellin, restrictocin, phenomycin, enomycin and the tricothecenes.

The present invention further contemplates antibody conjugated with a compound with nucleolytic activity (e.g. a ribonuclease or a DNA endonuclease such as a deoxyribonuclease; DNase) or other compound capable of damaging a cellular structure or organelle and therefore killing or diminishing the vitality of the cell.

The antibodies of the present invention may also be conjugated with a prodrug activating agent which converts a prodrug to an active anti-cancer drug. The agent component of such conjugates includes any agent capable of acting on a prodrug in such a way so as to convert it into its more active, cytotoxic form.

Alternatively, fusion proteins comprising at least the antigen binding region of an anti-CCR7 antibody of the invention linked to at least a functionally active portion of an enzyme of the invention can be constructed using recombinant DNA techniques well known in the art (see, e.g., Neuberger et al., 1984, Nature, 312:604-608).

Conjugates of the antibody and cytotoxic agent may be made using a variety of bifunctional protein coupling agents or linkers. The linker may be a "cleavable linker" facilitating release of the cytotoxic drug in the cell. For example, an acid-labile linker, peptidase-sensitive linker, dimethyl linker or disulfide-containing linker may be used. Alternatively, a fusion protein comprising the antibody and cytotoxic agent may be made, e.g. by recombinant techniques or peptide synthesis.

Production and Purification of the Antibodies of the Invention

Anti-CCR7 antibodies of the invention can be prepared by any of a number of conventional techniques. They will usually be produced in recombinant expression systems, using any technique known in the art. See e.g. Shukla and Thömmes (2010, "Recent advances in large-scale production of monoclonal antibodies and related proteins", Trends in Biotechnol. 28(5):253-261), Harlow and Lane (1988) "Antibodies: A Laboratory Manual", Cold Spring Harbor Laboratory Press, Cold Spring Harbor, NY, and Sambrook and Russell (2001) "Molecular Cloning: A Laboratory Manual ($3^{rd}$ edition), Cold Spring Harbor Laboratory, Cold Spring Harbor Laboratory Press, NY. Any expression system known in the art can be used to make the recombinant polypeptides of the invention. In general, host cells are transformed with a recombinant expression vector that comprises DNA encoding a desired polypeptide.

In one aspect the invention therefore relates to nucleic acid molecules comprising nucleotide sequences encoding an anti-CCR7 antibody of the invention. One nucleotide sequence encodes a polypeptide comprising at least the variable domain of the light chain of an anti-CCR7 antibody of the invention, another nucleotide sequence encodes a polypeptide comprising at least the variable domain of the heavy chain of an anti-CCR7 antibody of the invention. A preferred nucleic acid molecule is an expression vector wherein the nucleotide sequences encoding the antibody polypeptides of the invention are operably linked to expression regulatory sequences, such as e.g. a promoter and a signal sequence. Preferred signal sequences for expression of the anti-CCR7 antibody polypeptides of the invention include e.g. the heavy chain signal peptide: MGWTLVFLFLLSVTAGVHS (SEQ ID NO: 77) and the light chain signal peptide: MVSSAQFLGLLLLCFQGTRC (SEQ ID NO: 78).

In another aspect, the invention pertains to a cell comprising a nucleic acid molecule as defined above in this section. The cell preferably is an isolated cell or a cultured cell. Among the host cells that may be employed are prokaryotes, yeast or higher eukaryotic cells. Prokaryotes include gram negative or gram positive organisms, for example E. coli or bacilli. Higher eukaryotic cells include insect cells and established cell lines of mammalian origin. Examples of suitable mammalian host cell lines include the COS-7 line of monkey kidney cells (Gluzman et al., 1981, Cell 23:175), L cells, 293 cells, C127 cells, 3T3 cells, Chinese hamster ovary (CHO) cells, HeLa cells, BHK cell lines, and the CVI/EBNA cell line derived from the African green monkey kidney cell line CVI as described by McMahan et al., 1991, EMBO J. 10: 2821. Appropriate cloning and expression vectors for use with bacterial, fungal, yeast, and mammalian cellular hosts are described by Pouwels et al. (Cloning Vectors: A Laboratory Manual, Elsevier, New York, 1985).

The transformed cells can be cultured under conditions that promote expression of the polypeptide. Thus in one aspect the invention relates to a method for producing an anti-CCR7 antibody of the invention, the method comprising the step of cultivating a cell comprising at least one expression vector as defined herein, under conditions conducive to expression of the polypeptide and, optionally, recovering the polypeptide.

An anti-CCR7 antibody of the invention can be recovered by conventional protein purification procedures, including e.g. protein A-Sepharose, hydroxylapatite chromatography, gel electrophoresis, dialysis, or affinity chromatography (see e.g. Low et al., 2007, J. Chromatography B, 848:48-63; Shukla et al., 2007, J. Chromatography B, 848:28-39) including e.g. affinity chromatography using CaptureSelect™ ligands offer a unique affinity purification solution based on Camelid-derived single domain (VHH) antibody fragments (see e.g. Eifler et al., 2014. Biotechnology Progress DOI:10.1002/btpr.1958). Polypeptides contemplated for use herein include substantially homogeneous recombinant anti-CCR7 antibody polypeptides substantially free of contaminating endogenous materials.

Compositions Comprising the Antibodies of the Invention

In other aspect, the invention relates to a pharmaceutical composition comprising an anti-CCR7 antibody of the invention, i.e., an antibody, or antigen-binding fragment thereof, which binds to a CCR7 receptor, or a pharmaceutically derivative or prodrug thereof, together with a pharmaceutically acceptable carrier, adjuvant, or vehicle, for administration to a subject. Said pharmaceutical composition can be used in the methods of treatment described herein below by administration of an effective amount of the composition to a subject in need thereof. The term "subject", as used herein, refers to all animals classified as mammals and includes, but is not restricted to, primates and humans. The subject is preferably a male or female human of any age or race.

The term "pharmaceutically acceptable carrier", as used herein, is intended to include any and all solvents, dispersion media, coatings, antibacterial and antifungal agents, isotonic and absorption delaying agents, and the like, compatible with pharmaceutical administration (see e.g. "Handbook of Pharmaceutical Excipients", Rowe et al eds. 7$^{th}$ edition, 2012, www.pharmpress.com) The use of such media and agents for pharmaceutically active substances is well known in the art. Except insofar as any conventional media or agent is incompatible with the active compound, use thereof in the compositions is contemplated. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counterions such as sodium; metal complexes (e.g. Zn-protein complexes); and/or non-ionic surfactants such as TWEEN™ (polysorbate), PLURONICS™ (poloxamer) or polyethylene glycol (PEG).

The antibodies of the invention may be in the same formulation or may be administered in different formulations. Administration can be concurrent or sequential, and may be effective in either order.

Supplementary active compounds can also be incorporated into the pharmaceutical composition of the invention. Thus, in a particular embodiment, the pharmaceutical composition of the invention may also contain more than one active compound as necessary for the particular indication being treated, preferably those with complementary activities that do not adversely affect each other. For example, it may be desirable to further provide a chemotherapeutic agent, a cytokine, an analgesic agent, or an immunomodulating agent, e.g. an immunosuppressive agent or an immunostimulating agent. The effective amount of such other active agents depends, among other things, on the amount of antibody of the invention present in the pharmaceutical composition, the type of disease or disorder or treatment, etc.

In an embodiment, the antibody of the invention is prepared with carriers that will protect said compound against rapid elimination from the body, such as a controlled release formulation, including implants and microencapsulated delivery systems, e.g. liposomes. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions, including targeted liposomes can also be used as pharmaceutically acceptable carriers. These can be prepared according to methods known to those skilled in the art, for example, as described in U.S. Pat. No. 4,522,811, WO2010/095940.

The administration route of the antibody (or fragment thereof) of the invention can be oral, parenteral, by inhalation or topical. The term "parenteral" as used herein includes intravenous, intra-arterial, intralymphatic, intraperitoneal, intramuscular, subcutaneous, rectal or vaginal administration. The intravenous forms of parenteral administration are preferred. By "systemic administration" is meant oral, intravenous, intraperitoneal and intramuscular administration. The amount of an antibody required for therapeutic or prophylactic effect will, of course, vary with the antibody chosen, the nature and severity of the condition being treated and the patient. In addition, the antibody may suitably be administered by pulse infusion, e.g., with declining doses of the antibody. Preferably the dosing is given by injections, most preferably intravenous or subcutaneous injections, depending in part on whether the administration is brief or chronic.

Thus, in a particular embodiment, the pharmaceutical composition of the invention may be in a form suitable for parenteral administration, such as sterile solutions, suspensions or lyophilized products in the appropriate unit dosage form. Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor®EM (Polyoxyl-35 castor oil) (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyethylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol or sodium chloride in the composition.

Prolonged absorption of the injectable compositions can be brought about by including in the composition an agent which delays absorption, for example, aluminium monostearate and gelatin.

Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

In a particular embodiment, said pharmaceutical composition is administered via intravenous (IV) or subcutaneous (SC). Adequate excipients can be used, such as bulking agents, buffering agents or surfactants. The mentioned formulations will be prepared using standard methods for preparing parenterally administrable compositions as are well known in the art and described in more detail in various sources, including, for example, "Remington: The Science and Practice of Pharmacy" (Ed. Allen, L. V. 22nd edition, 2012, www.pharmpress.com).

It is especially advantageous to formulate the pharmaceutical compositions, namely parenteral compositions, in dosage unit form for ease administration and uniformity of dosage. Dosage unit form as used herein refers to physically discrete units suited as unitary dosages for the subject to be treated; each unit containing a predetermined quantity of active compound (antibody of the invention) calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Generally an effective administered amount of an antibody of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.001 to 1,000 mg/kg body weight/day, preferably about 0.01 to about 100 mg/kg body weight/day, most preferably from about 0.05 to 10 mg/kg body weight/day.

Aside from administration of antibodies to the patient, the present application contemplates administration of antibodies by gene therapy. WO96/07321 relates the use of gene therapy to generate intracellular antibodies.

The pharmaceutical compositions can be included in a container, pack, or dispenser together with instructions for administration.

The antibodies and pharmaceutical compositions of this invention may be used with other drugs to provide a combination therapy. The other drugs may form part of the same composition, or be provided as a separate composition for administration at the same time or at different time.

Use of the Antibodies of the Invention

The antibodies and pharmaceutical compositions of the invention will be useful in the treatment of a wide range of diseases, conditions, and indications. Examples of types of diseases that can be treated include cancerous conditions, inflammatory conditions, conditions and complications arising from tissue or organ transplantation, as well as conditions and complications arising from or associated with fibrosis.

The antibodies and pharmaceutical compositions of the invention can suitably be used for treating disorders or diseases associated with cancers, specially, for treating cancers said cancers being characterized by tumour cells expressing a CCR7 receptor, more specifically, for killing or inducing apoptosis of tumour cells expressing a CCR7 receptor. Illustrative, non-limitative, cancers which tumour cells express a CCR7 receptor susceptible of being treated according to the invention include chronic lymphocytic leukaemia (CLL), mantle cells lymphoma (MCL), follicular lymphoma, large B-cell lymphoma, AIDS-associated lymphoma, lymphoplasmacytic lymphoma, Burkitt lymphoma, B-cell acute lymphoblastic leukaemia, Hodgkin's disease, adult T-cell leukaemia/lymphoma, mycosis fungoides, blast crisis of chronic myeloproliferative syndromes, blast crisis of myelodysplastic syndromes, breast cancer, non-small cell lung cancer, melanoma, gastric cancer or squamous cell carcinoma of the head and neck and colon carcinoma. In a preferred embodiment, cancers susceptible of being treated according to the invention include breast cancer, non-small cell lung cancer, melanoma, gastric cancer or squamous cell carcinoma of the head and neck and colon carcinoma. In a most preferred embodiment, cancers susceptible of being treated according to the invention include follicular lymphoma, adult T-cell leukaemia/lymphoma, Burkitt lymphoma, blast crisis of chronic myeloproliferative syndromes and blast crisis of myelodysplastic syndromes. In a still most preferred embodiment, cancers to be treated according to the invention include CLL and MCL.

In a particular embodiment, the antibody of the invention may be combined with other treatments of the medical conditions described herein, e.g., chemotherapy, radiation therapy, immunotherapy, or surgical method, including alkylating agents, antimetabolites, antihormones, therapeutic for various symptoms, e.g., painkillers, diuretics, antidiuretics, antivirals, antibiotics, cytokines, nutritional supplements, anemia therapeutics, blood clotting therapeutics, bone therapeutics, psychiatric and psychological therapeutics, and the like.

Bone marrow or peripheral blood stem cells may be harvested from said patient subsequent to treatment with anti-CCR7 antibody in order to effect autologous bone marrow or stem cell transplantation.

It may also be useful to treat patients with cytokines in order to up-regulate the expression of CCR7 or other target protein on the surface of cancerous B cells prior to administration of an antibody of the invention. Cytokines may also be administered simultaneously with or prior to or subsequent to administration of the depleting antibody or radiolabelled antibody in order to stimulate immune effector functions.

In one embodiment, chemotherapeutic regimens may be used to supplement the therapies disclosed herein, and may be administered simultaneously with or sequentially in any order with administration of said radiolabelled antibody. The chemotherapy regimen may be selected from the group consisting of CHOP (cyclophosphamide, doxorubicin (also called hydroxyl daunorubicin), vincristine (also called oncovin) and prednisone), ICE (idarubicin, cytarabine and etoposide), Mitozantrone, Cytarabine, DVP (daunorubicin, vincristine and prednisone), ATRA (all-trans retinoic acid), Idarubicin, hoelzer chemotherapy regime, La chemotherapy regime, ABVD (bleomycin, dacarbazine, doxorubicin and vincristine), CEOP (cyclophosphamide, epirubicin, vincristine and prednisolone), 2-CdA (2-chlorodeoxyadenosine), FLAG & IDA (fludarabine, cytarabine, filgastrim and idarubicin), (with or without subsequent G-CSF (granulocyte-colony stimulating factor) treatment), VAD (vincristine, doxorubicine and dexamethasone), M & P (melphlan and prednisone), C (cyclophosphamide)-Weekly, ABCM (adriamycin, bleomycin, cyclophosphamide and mitomycin-C), MOPP (mechlorethamine, vincristine, prednisone and procarbazine) and DHAP (dexamethasone, cytarabine and cisplatin). A preferred chemotherapeutic regimen is CHOP.

Thus, in another aspect, the disclosure relates to a method for treating cancer, specifically a cancer of which the tumour cells express a CCR7 receptor, which method comprises administering to a subject in need of said treatment a therapeutically effective amount of an antibody of the invention, i.e., an antibody, or antigen-binding fragment thereof, which binds to the CCR7 receptor, or a pharmaceutical composition of the invention. In a particular embodiment, said cancer is a cancer characterized by tumour cells expressing a CCR7 receptor. Illustrative, non-limitative, cancers to be treated according to the invention include CLL, MCL, follicular lymphoma, large B-cell lymphoma, AIDS-associated lymphoma, lymphoplasmacytic lymphoma, Burkitt lymphoma, B-cell acute lymphoblastic leukaemia, Hodgkin's disease, adult T-cell leukaemia/lymphoma, mycosis fungoides, blast crisis of chronic myeloproliferative syndromes, blast crisis of myelodysplastic syndromes, breast cancer, non-small cell lung cancer, melanoma, gastric cancer or squamous cell carcinoma of the head and neck and colon carcinoma. In a preferred embodiment, cancers to be treated according to the invention include breast cancer, non-small cell lung cancer, melanoma, gastric cancer or squamous cell carcinoma of the head and neck and colon carcinoma. In a most preferred embodiment, cancers to be treated according to the invention include follicular lymphoma, adult T-cell leukaemia/lymphoma, Burkitt lymphoma, blast crisis of chronic myeloproliferative syndromes and blast crisis of myelodysplastic syndromes. In a still most preferred embodiment, cancers to be treated according to the invention include CLL and MCL.

In other aspect, the invention relates to an in vitro method for killing or for inducing apoptosis of tumour cells expressing a CCR7 receptor which comprises contacting said cells with an antibody of the invention, i.e., an antibody, or antigen-binding fragment thereof, which binds to a CCR7 receptor. In a particular embodiment, said tumour cells are tumour cells expressing a CCR7 receptor, such as CLL and MCL cells.

An antibody that "inhibits the growth of tumor cells expressing a CCR7 polypeptide" or a "growth inhibitory" antibody is one which results in measurable growth inhibition of cancer cells expressing or overexpressing the appropriate polypeptide. The CCR7 polypeptide is a transmembrane polypeptide expressed on the surface of a cancer cell. Preferred growth inhibitory anti-CCR7 antibodies inhibit growth of CCR7-expressing tumor cells by greater than 20%, preferably from about 20% to about 50%, and even more preferably, by greater than 50% (e.g., from about 50% to about 100%) as compared to the appropriate control, the control typically being tumor cells not treated with the antibody being tested. In one embodiment, growth inhibition can be measured at an antibody concentration of about 0.1 to 30 mg/ml or about 0.5 nM to 200 nM in cell culture, where the growth inhibition is determined 1-10 days after exposure of the tumor cells to the antibody. Growth inhibition of tumor cells in vivo can be determined in various ways such as is described in EP2474557B1 for tumor cells expressing CCR7. The antibody is growth inhibitory in vivo if administration of the anti-CCR7 antibody at about 1 mg/kg to about 100 mg/kg body weight results in reduction in tumor size or tumor cell proliferation within about 5 days to 3 months from the first administration of the antibody, preferably within about 5 to 30 days.

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is usually one which overexpresses a CCR7 polypeptide. Preferably the cell is a tumor cell, e.g., a hematopoietic cell, such as a B cell, T cell, basophil, eosinophil, neutrophil, monocyte, platelet or erythrocyte. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody which induces apoptosis is one which results in about 2 to 50 fold, preferably about 5 to 50 fold, and most preferably about 10 to 50 fold, induction of annexin binding relative to untreated cell in an annexin binding assay.

An antibody which "induces cell death" is one which causes a viable cell to become nonviable. The cell is one which expresses a CCR7 polypeptide and is of a cell type which specifically expresses or overexpresses a CCR7 polypeptide. The cell may be cancerous or normal cells of the particular cell type. The CCR7 polypeptide may be a transmembrane polypeptide expressed on the surface of a cancer cell or may be a polypeptide that is produced and secreted by a cancer cell. The cell may be a cancer cell, e.g., a B cell or T cell. Cell death in vitro may be determined in the absence of complement and immune effector cells to distinguish cell death induced by antibody-dependent cell-mediated cytotoxicity (ADCC) or complement dependent cytotoxicity (CDC). Thus, the assay for cell death may be performed using heat inactivated serum (i.e., in the absence of complement) and in the absence of immune effector cells. To determine whether the antibody is able to induce cell death, loss of membrane integrity as evaluated by uptake of propidium iodide (PI), trypan blue (see Moore et al. Cytotechnology 17:1-11 (1995)) or 7AAD can be assessed relative to untreated cells. Preferred cell death-inducing antibodies are those which induce PI uptake in the PI uptake assay in BT474 cells.

Information concerning tumour cells expressing a CCR7 receptor susceptible of being treated with the methods of the invention, antibodies, administration regimens and dosages have been previously mentioned. In a particular embodiment, tumour cells expressing a CCR7 receptor susceptible of being treated with the above mentioned methods are CLL or MCL cells.

In all the cases, the expression "therapeutically effective amount" means an amount effective in treating cancer, as previously defined; said amount can be an amount sufficient to effect a desired response, or to ameliorate a symptom or sign, e.g., of metastasis or primary tumour progression, size, or growth. A therapeutically effective amount for a particular subject may vary depending on factors such as the condition being treated, the overall health of the subject, the method, route, and dose of administration and the severity of side effects. Preferably, the effect will result in a change in quantifying of at least about 10%, preferably at least 20%, 30%, 50%, 70%, or even 90% or more. When in combination, a therapeutically effective amount is in ratio to a combination of components and the effect is not limited to individual components alone. A therapeutically effective amount will modulate the symptoms typically by at least about 10%; usually by at least about 20%; preferably at least about 30%; or more preferably at least about 50%. Alternatively, modulation of migration will mean that the migration or trafficking of various cell types is affected. Such will result in, e.g., statistically significant and quantifiable, changes in the numbers of cells being affected. This may be a decrease in the numbers of target cells being attracted within a time period or target area. Rate of primary tumour progression, size, dissemination or growth may also be monitored.

The anti-CCR7 antibodies and compositions of the invention comprising such antibodies can also be used to treat inflammatory conditions and conditions and complications arising from tissue or organ transplantation.

CCR7 activity is implicated in inflammatory bowel diseases (IBDs) such as Crohn's disease and ulcerative colitis. Crohn's disease is chronic and debilitating inflammatory bowel disease that is thought to reflect an overly-active TH1-mediated immune response to the flora of the gut. The lesions of Crohn's disease can appear anywhere in the bowel and occasionally elsewhere in the gastrointestinal tract. Ulcerative colitis lesions, on the other hand, usually appear in the colon. The nature of the lesions is also different, but the diseases are sufficiently similar that is sometimes difficult to distinguish them clinically. See, e.g., U.S. Pat. No. 6,558,661. The antibodies and compositions described herein can be used to treat IBD patients, and/or reduce, prevent, or eliminate one or more symptoms or complications of IBD.

Inhibition of CCR7 activity has been implicated in tissue or organ transplant rejection (Lo et al., 25 2011, Transplantation 91:70-77; Liu et al., 2011, Eur J Immunol 41:611-23; Yuling et al., Am J Transplant 8:1401-12). The antibodies and compositions described herein can be used to treat tissue or organ transplant recipients, for example, kidney, heart, skin, or lung transplant recipients, and/or reduce, prevent, or eliminate one or more complications of transplant surgery.

CCR7 activity has been implicated in asthma, allergic airway inflammation, airway smooth muscle hyperplasia, and fibrotic lung diseases (Gomperts et al., 2007, J Leukoc Biol. 82:449-56; Kawakami et al., 2012, Cell Immunol 2575:24-32; Saunders et al., 2009, Clin Exp Allergy 39:1684-92). The antibodies and compositions described herein can be used to treat patients with asthma, allergic airway inflammation, airway smooth muscle hyperplasia, or fibrotic lung diseases, and/or to reduce, prevent, or eliminate one or more symptoms or complications of these diseases.

CCR7 activity has been implicated in rheumatoid arthritis (Moschovakis et al., 2012, Eur J Immunol. 42:1949-55). The antibodies and compositions described herein can be used to treat patients with rheumatoid arthritis, and/or to reduce, prevent, or eliminate one or more symptoms or complications of rheumatoid arthritis.

CCR7 activity has been implicated in multiple sclerosis (Aung et al., 2010, J Neuroimmunol. 226:158-64). The antibodies and compositions described herein can be used to treat patients with multiple sclerosis, and/or to reduce, prevent, or eliminate one or more symptoms or complications of multiple sclerosis.

CCR7 activity has been implicated in psoriasis (Fan et al., 2008, Indian J Dermatol Venereol Leprol. 74(5):550; Bosè et al., 2013, Am J Pathol, 183(2):413-421). The antibodies and compositions described herein can be used to treat patients with psoriasis, and/or to reduce, prevent, or eliminate one or more symptoms or complications of psoriasis.

CCR7 activity has been implicated in atherosclerosis (Luchtefeld et al., 2010, Circulation 10 122:1621-28). The antibodies and compositions described herein can be used to treat patients with atherosclerosis, and/or to reduce, prevent, or eliminate one or more symptoms or complications of atherosclerosis.

CCR7 activity has been implicated in HIV infection (Evans et al., 2012, Cytokine Growth Factor Rev. 23:151-57). The antibodies and compositions described herein can be used to treat patients infected with HIV, including patients having AIDS, or patients at risk of contracting HIV or of developing AIDS, and/or to reduce, prevent, or eliminate one or more symptoms or complications of HIV or AIDS.

The anti-CCR7 antibodies of the invention and compositions comprising such antibodies can further be used for the therapy of fibrosis, preferably tissue fibrosis. An example of the tissue fibrosis includes fibrosis selected from the group consisting of hepatic fibrosis, renal fibrosis, pulmonary fibrosis, skin fibrosis, cardiovascular fibrosis, gastrointestinal fibrosis and other fibrous diseases. An example of the hepatic fibrosis includes hepatic fibrosis selected from the group consisting of hepatic cirrhosis, ischemic reperfusion, post-hepatic transplant disorder, necrotic hepatitis, hepatitis B, hepatitis C, primary biliary cirrhosis, and primary sclerosing cholangitis. As to the hepatic cirrhosis, one caused by at least one selected from the group consisting of induction by alcohol, induction by a drug, and induction by chemical induction is recited. An example of the renal fibrosis includes renal fibrosis selected from the group consisting of proliferative glomerulonephritis, sclerotic glomerulonephritis, nephrogenic fibrosing dermopathy, diabetic nephropathy, renal tubule interstitial fibrosis, and focal segmental glomerulosclerosis. An example of the pulmonary fibrosis includes pulmonary fibrosis selected from the group consisting of pulmonary interstitial fibrosis, drug induced sarcoidosis, pulmonary fibrosis, idiopathic pulmonary fibrosis, asthma, chronic obstructive pulmonary disease, diffuse pulmonary alveolar injury disease, pulmonary hypertension, and neonatal bronchopulmonary dysplasia. An example of the skin fibrosis includes skin fibrosis selected from the group consisting of scleroderma, keloid scarring, psoriasis, hypertrophic scarring, and pseudo scleroderma. An example of the cardiovascular fibrosis includes cardiovascular fibrosis selected from the group consisting of atherosclerosis, coronary restenosis, congestive cardiomyopathy, heart failure, cardiac transplantation, and myocardial fibrosis. An example of the gastrointestinal fibrosis includes gastrointestinal fibrosis selected from the group consisting of collagenous colitis, villous atrophy, crypt hyperplasia, polyp formation, fibrosis of Crohn's disease, gastric ulcer healing, and post-abdominal adhesion surgery scar. The fibrosis may have a condition arising from bone-related fibro sing disease and may be rheumatoid pannus formation.

Any of the above mentioned therapeutic methods described above may be applied to any subject in need of such therapy, including, for example, mammals, preferably primates, and most preferably, humans.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

DESCRIPTION OF THE FIGURES

FIG. 2B: CCL21) on migration of human T-cell lymphoma cells is inhibited by the murine anti-CCR7 mAb 730 ($IC_{50}$: 15 nM and 6 nM respectively).

EXAMPLES

1. Generation of Mouse Anti-CCR7 mAbs

Normal mice (i.e., mice with a murine immune system) were immunized with antigens comprising or expressing amino acid sequences from the human CCR7 N-terminal extracellular domain. Mouse monoclonal antibodies were obtained using standard hybridoma technology.

Initial attempts using antigens lacking sulfation at $Y_{41}$ of the CCR7 N-terminal domain produced antibodies that failed to neutralize CCL19- or CCL21-dependent CCR7 signalling. Immunization with antigens comprising sulfation of $Y_{41}$ produced a series of mouse monoclonal antibodies that were capable of neutralizing CCL19- or CCL21-dependent CCR7 signalling. For eight selected mouse anti-human CCR7 monoclonal antibodies sequences were determined. The amino acid sequences of the hypervariable regions of these eight monoclonal antibodies are listed in Table 1.

The amino acid sequence of the variable domains of the heavy and light chains of the 729 mouse antibody are given in SEQ ID NO.'s: 1 and 2, respectively.

TABLE 1

Amino acid sequences of the hypervariable regions of eight selected mouse anti-human CCR7 monoclonal antibodies.

| Antibody | HVR-H1 amino acid sequence | SEQ ID NO |
|---|---|---|
| 726 | GFTFSDYA | 3 |
| 727 | GFAFSSYA | 4 |
| 728 | GFAFSNYA | 5 |
| 729 | GLTFRDFA | 6 |
| 730 | GFPFSNYA | 7 |
| 731 | GFTFTDYA | 8 |
| 734 | GFTFSNYA | 9 |
| 737 | GFTFSSYA | 10 |

| Antibody | HVR-H2 amino acid sequence | SEQ ID NO |
|---|---|---|
| 726 | ISDGGSHT | 11 |
| 727 | ISDGGTYP | 12 |
| 728 | ISDGGTYP | 12 |
| 729 | ISSGGFYT | 13 |
| 730 | ISSGGSYT | 14 |
| 731 | ISDRGSFT | 15 |
| 734 | ISSGGSHT | 16 |
| 737 | ISSGGSYT | 14 |

| Antibody | HVR-H3 amino acid sequence | SEQ ID NO |
|---|---|---|
| 726 | GRRAGRYD---ERDAMDY | 17 |
| 727 | TRRAYRYD---VKNSMDY | 18 |
| 728 | TRRAYRYD---VKNSMDY | 18 |
| 729 | VRRAYRYDGTGDYSALDY | 19 |
| 730 | ARREYRY----AENAMDY | 20 |
| 731 | TRRAYRYD---GDNAMDY | 21 |
| 734 | ARRAYRYD---EDSAMDS | 22 |
| 737 | ARATTVV-----GTDFDY | 23 |

| Antibody | HVR-L1 amino acid sequence | SEQ ID NO |
|---|---|---|
| 726 | SSVSSSY | 24 |
| 727 | QDIGDN | 25 |
| 728 | QDIGNN | 26 |
| 729 | QDIGPS | 27 |
| 730 | QDIGDN | 24 |
| 731 | QDIGGS | 28 |
| 734 | QSLLDSDGKTY | 29 |
| 737 | QDIGSS | 30 |

TABLE 1-continued

Amino acid sequences of the hypervariable regions of eight selected mouse anti-human CCR7 monoclonal antibodies.

| Antibody | HVR-L2 amino acid sequence | SEQ ID NO |
|---|---|---|
| 726 | SIS | 32 |
| 727 | ATS | 31 |
| 728 | ATS | 31 |
| 729 | ATS | 31 |
| 730 | ATS | 31 |
| 731 | ATS | 31 |
| 734 | LVS | 33 |
| 737 | ATS | 31 |

| Antibody | HVR-L3 amino acid sequence | SEQ ID NO |
|---|---|---|
| 726 | QQWSSNPPT | 34 |
| 727 | LQYASSPLT | 35 |
| 728 | LQYASSPLT | 35 |
| 729 | LQFASSPLT | 36 |
| 730 | LQYASSPLT | 35 |
| 731 | LQYANSPLT | 37 |
| 734 | WQGTHFPQT | 38 |
| 737 | LQYASSPPT | 39 |

2. Evaluation of Mouse Anti-CCR7 mAbs 2.1 Epitope Mapping

Figure 1A:
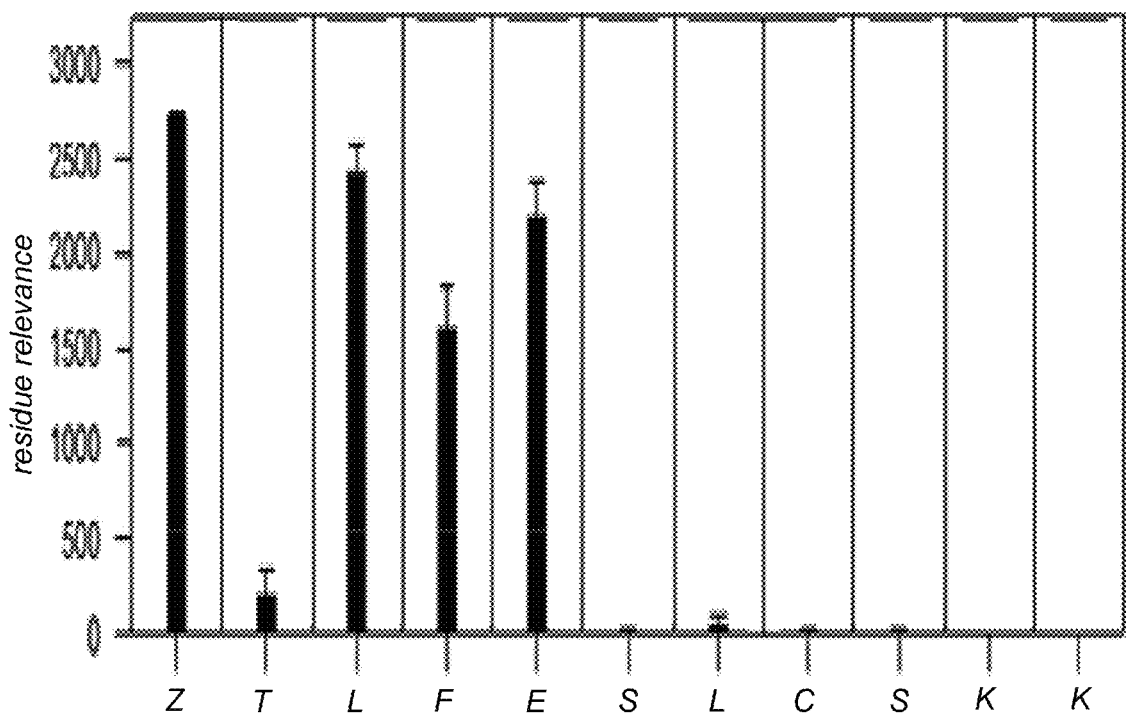
FIG. 1A-FIG. 1B. Epitope mapping of FIG. 1A murine mAbs 729 and FIG. 1B humanized mAb 650 (the humanized version of mAb 729). Both antibodies recognize the same linear epitope located on the N-terminus of human CCR7 (Z=sulfated Tyr).
Figure 1B:
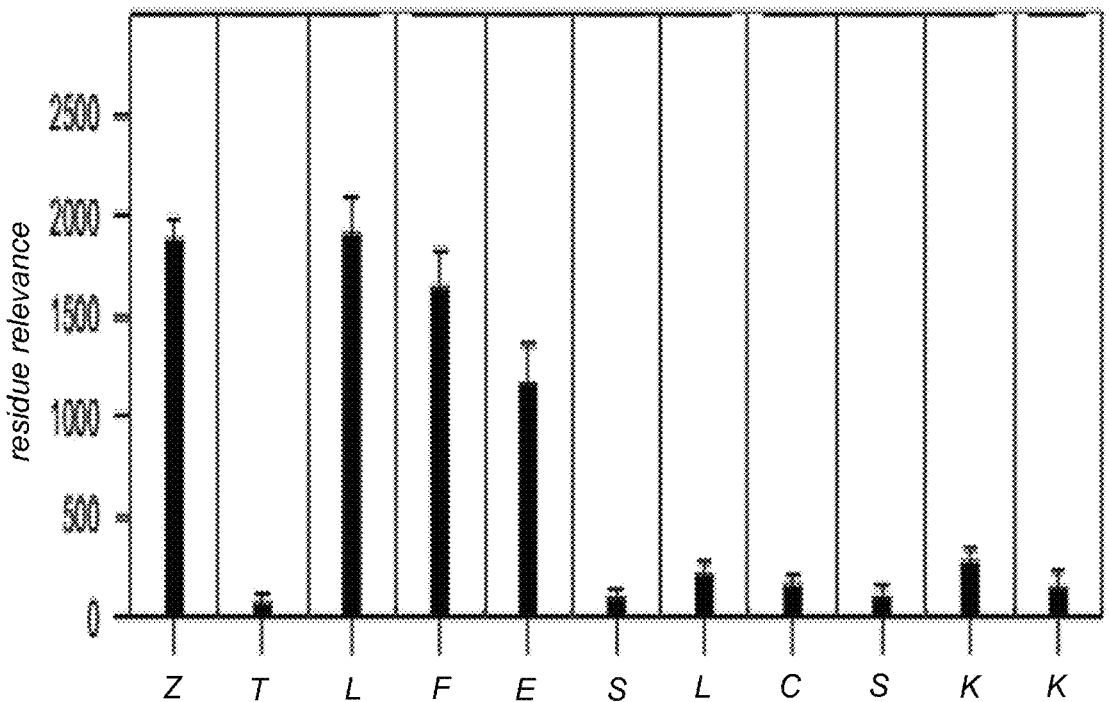

Epitope mapping of monoclonal antibodies (FIG. 1A-FIG. 1B) was performed according to previously published protocols (Slootstra et al., 1996 Mol Divers, 1:87-96; Timmerman et al., 2007, J Mol Recognit, 20:283-99). In short: The binding of antibody to each peptide is tested in an ELISA based PEPSCAN. The peptide arrays are incubated with a primary antibody solution, for example consisting of 1 mg/ml diluted in blocking solution (4% horse serum, 5% ovalbumin (w/v) in PBS/1% TWEEN Polysorbate). After washing, the peptides are incubated with a 1000-fold dilution of antibody peroxidase conjugate for one hour at 25° C. After washing, the peroxidase substrate solution (0.5 mg/ml 2,2'-azino-di-3-ethylbenzthiazoline sulfonate (ABTS) and 0.006% $H_2O_2$ in 0.05 M citrate buffer pH 4) was added. After one hour incubation at room temperature, the colour development was measured. The colour development was quantified with a charge coupled device (CCD)—camera and an image processing system.

2.2 Anti-CCR7 mAbs Inhibit CCR7-Dependent Intracellular Signalling

The obtained anti-CCR7 monoclonal antibodies (Table 2) inhibit the CCL19 and CCL21 mediated intracellular signalling in human CCR7 overexpressing Chinese Hamster Ovary (CHO) cells, as determined by an established standard β-arrestin recruitment assay (PathHunter™, DiscoverX, Fremont, CA, USA; Southern et al., 2013, J Biomol Screen. 18(5):599-609).

TABLE 2

Inhibition of CCL19 and CCL21 mediated intracellular signalling in human CCR7 overexpressing Chinese Hamster Ovary (CHO) cells as determined by a β-arrestin recruitment assay.

| Mab | IC$_{50}$ β-arrestin (nM) | |
|---|---|---|
| | CCL19 | CCL21 |
| mAb 726 | 482 | 166 |
| mAb 727 | 30 | 11 |
| mAb 728 | 37 | 27 |
| mAb 729 | 43 | 16 |
| mAb 730 | 23 | 11 |
| mAb 731 | 38 | 15 |
| mAb 732 | 131 | 29 |
| mAb 733 | 599 | 60 |
| mAb 734 | 88 | 31 |
| mAb 735 | 113 | 17 |

2.3 Anti-CCR7 mAb Inhibits Cell Migration

Figure 2A:
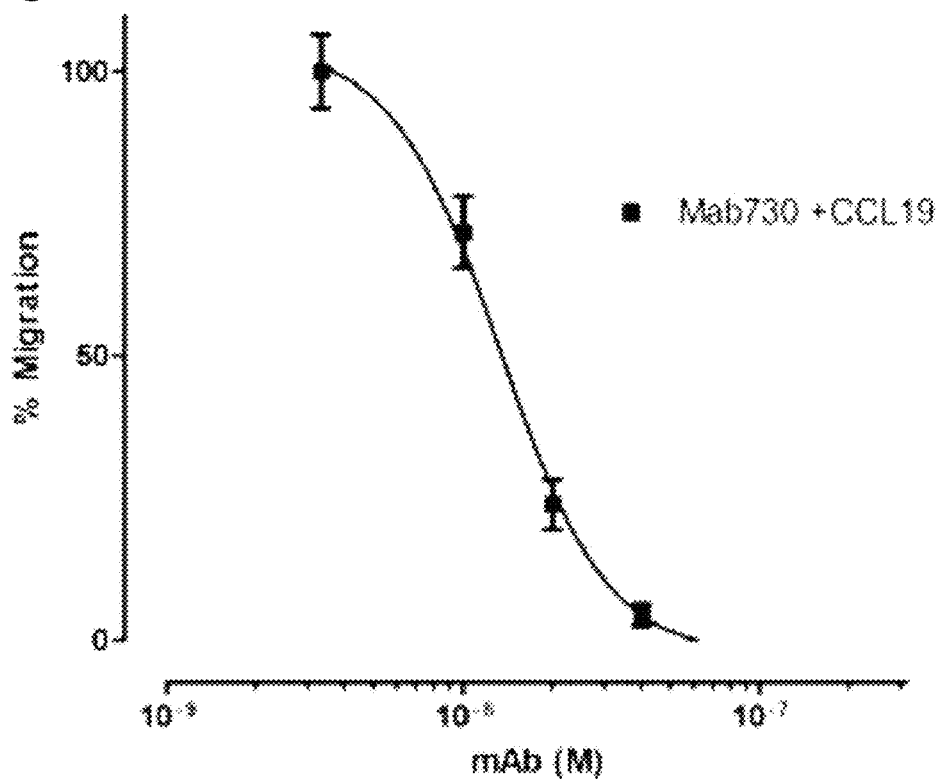
FIG. 2A-FIG. 2B. The agonistic effect of ligand binding (FIG. 2A: CCL19.
Figure 2B:
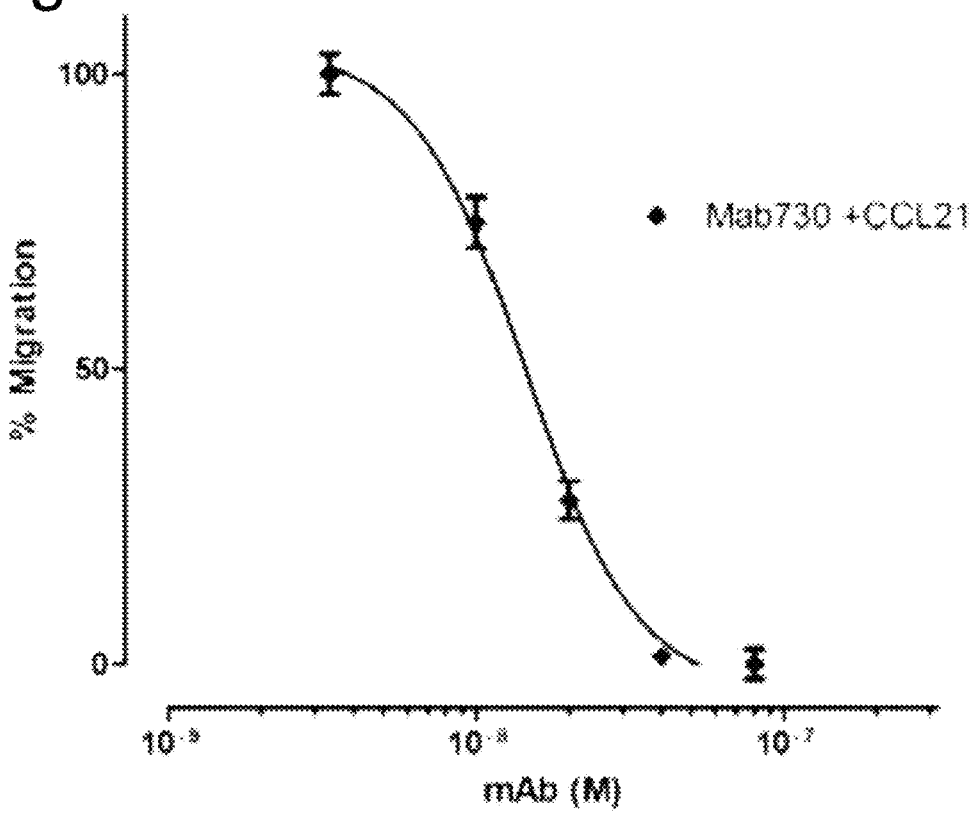

Murine mAb 730 inhibits the migration (chemotaxis) of human T cell lymphoma cells, endogenously expressing the human CCR7 receptor, induced by ligands CCL19 and CCL21, with an IC$_{50}$ of 15 nM and 6 nM, respectively (FIG. 2A-FIG. 2B).

Cell migration assays were performed using transwell double chambers with inserts of 8 μm pore size (Costar, Cambridge, MA, USA). The lower chamber contained the ligand (CCL19 or CCL21) diluted in HamF12 medium supplemented with 0.5% BSA. The CCR7 endogenous expressing cells (T-cell lymphoma (HuT-78), pre-incubated with anti CCR7 monoclonal antibodies, were placed into the insert and the chamber assembly was incubated at 37° C. The amount of transmembrane migrated cells in the lower chamber was determined, after cell lysis, by DNA staining (CyQuant GR dye solution, Life Technologies Ltd, UK).

2.4 Anti-CCR7 mAb Block CCR7 Signalling with No Agonistic Effects

Tested at high concentrations (267 nM), none of the murine anti-human CCR7 binding monoclonal antibodies listed in Table 2 above, including mAb 729 and 730, induced detectable intracellular agonistic effects in human CCR7 overexpressing Chinese Hamster Ovary (CHO) cells as determined by an established standard β-arrestin recruitment assay (PathHunter™, DiscoverX, Fremont, CA, USA; Southern et al., 2013, J Biomol Screen. 18(5):599-609) (data not shown). IgG2a was used as negative control, and CCL21, a natural ligand for CCR7, was used as positive control.

2.5 Affinity Measurements

2.5.1 Biacore Affinity Measurement

The affinities of the identified monoclonal antibodies were determined by Biacore measurements under standard conditions. The monoclonal antibody was immobilized on an appropriate sensor surface and the solution of the sulfated antigen SYM1899 ((pyroGlu)DEVTDDZIGDNTTVDZTLFESLCSKKDVRNK; SEQ ID NO: 76); wherein Z denotes sulfated Tyrosine) comprising residues 19-49 derived from the N-terminus of human CCR7, was passed over the sensor surface. The obtained affinity value (Kd) of murine mAb 729 for SYM1899 was 0.7 nM.

2.5.2 Flow Cytometry Affinity Measurement

Human CCR7 expressing CHO cells (10$^6$ cells/ml) were pre-incubated at 4° C. for 24 hours with murine mAbs 726-735 at a 3-fold dilution series (range 20 nM-0.11 pM). The amount of bound antibody was determined by staining with secondary mouse-specific antibody labelled with Phycoerythrin (PE) and subsequent detection by flow cytometry. The EC$_{50}$ values (Table 3 were determined from the sigmoid binding curves at 50% of the minimum and maximum plateau values.

TABLE 3

Affinity values (EC$_{50}$) of murine anti-humanCCR7 mAbs for hCCR7 expressing CHO cells, determined by flow cytometry.

| mAb | 726 | 727 | 728 | 729 | 730 | 731 | 732 | 733 | 734 | 735 |
|---|---|---|---|---|---|---|---|---|---|---|
| EC50 (nM) | 13.9 | 4.2 | 7.0 | 2.4 | 5.1 | 4.6 | 4.3 | 3.8 | 4.6 | 3.9 |

2.6 Anti-CCR7 mAb is Safe on Normal Cells

Figure 3:
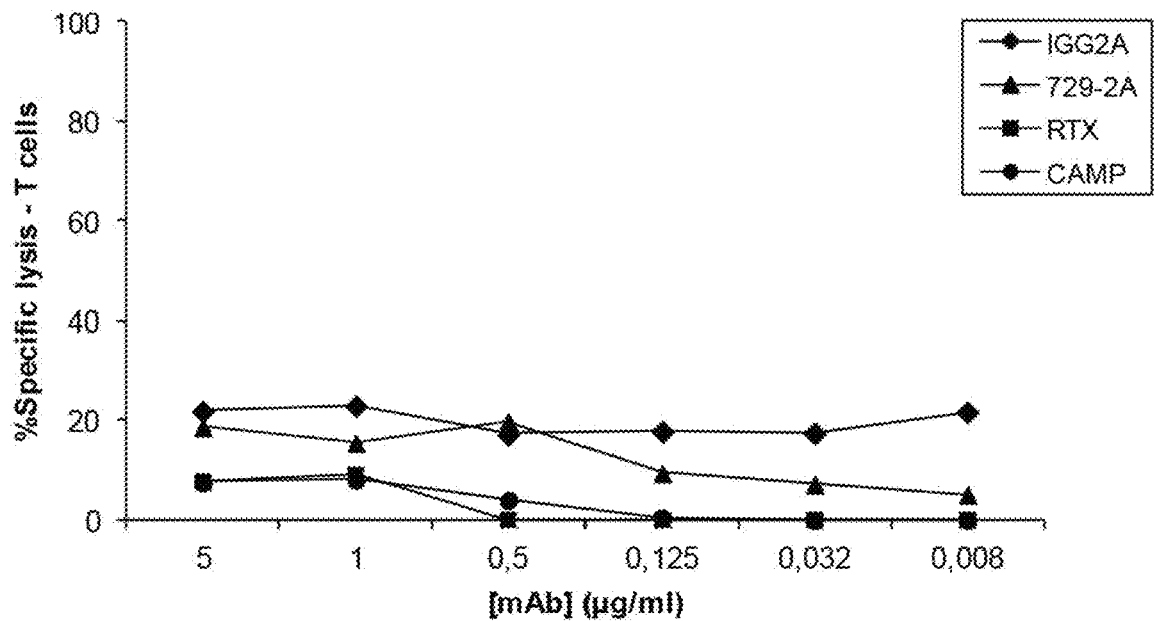
FIG. 3. Tested in a CDC-assay, normal naïve human T-cells are not killed by treatment with anti-human CCR7 mAb 729-2A (triangle), neither by RITUXAN® (Rituximab) (RTX; square) nor CAMPATH® (Alemtuzumab) (CAMP; circle). IgG2A (diamond) was included as negative control.

In CDC-assays normal naïve human T-cells (FIG. 3) are safe for treatment with anti-CCR7 monoclonal antibody mAb 729-2A, at effective concentrations (range 33-0.5 nM. The CDC assays were performed as described by Cuesta-Mateos et al. (2015, Cancer Immunol Immunother. DOI: 10.1007/s00262-015-1670-z).

2.7 Anti-CCR7 mAb Kills CD20-Refractory CLL Patient Tumor Cells

Figure 4:
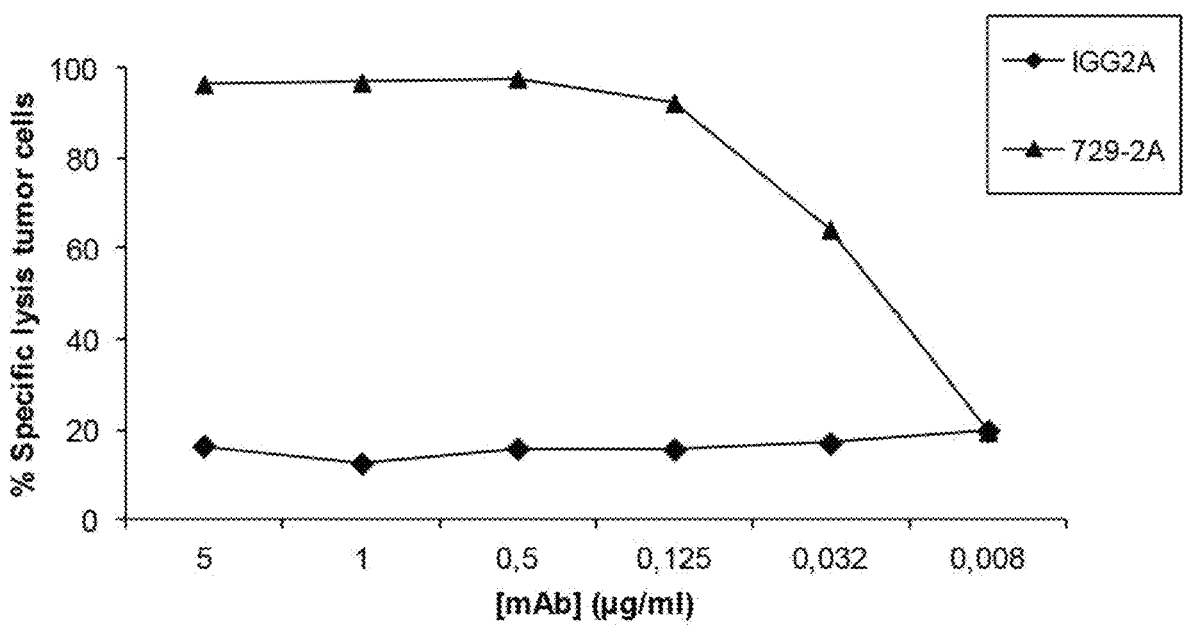
FIG. 4. CDC-assay. CD20-refractory CLL patient tumor cells are killed by murine anti-humanCCR7 mAb729-2A (729-2A; triangle), but not by negative control IgG2A (diamond).

CD20-refractory CLL tumor B-cells, from a patient unresponsive to cytostatics and anti CD-20 monoclonal antibody therapy and considered to be anti-CD20 therapy resistant, are efficiently killed in the complement dependent cytotoxicity (CDC) assay by mAb729-2A (IC$_{50}$ 0.15 nM) (FIG. 4). The CDC assays were performed as described by Cuesta-Mateos et al. (2015, supra).

3. Humanization

3.1 Design and Construction of Humanized Ab's

The murine monoclonal antibody anti-human CCR7 MAb 729 was selected for humanization. Using antibody numbering systems from IMGT and Kabat, the CDRs were identified in mAb 729 (see Table 1 above). These two numbering systems identify different residues of the murine antibody as belonging to the CDR, and a combined IMGT/Kabat CDR sequence was used for optimal retention of CDR-loop conformation. The code for the humanized variants of murine mAb 729 as used herein is mAb 650.

For the murine heavy chain, the closest human germ line gene V-region is *Homo sapiens* IGHV3-21 (SEQ ID NO: 73). For the murine light chain, the closest human germ line gene V-region is *Homo sapiens* IGKV1-39 (SEQ ID NO: 74).

For humanization of the heavy chain, online databases of Human IgG sequences were searched for comparison to the murine VH domain using BLAST search algorithms, and candidate human variable domains selected from the top 200 BLAST results. These were reduced to three candidates based on a combination of framework homology, maintaining key framework residues and canonical loop structure, respectively CAG17616 (SEQ ID NO: 67), AAL67510 (SEQ ID NO: 68) and ACS96226 (SEQ ID NO: 69). With the CDRs of the murine anti-human CCR7 MAb 729 VH grafted into these acceptor frameworks they become the humanized variants VH1, VH2 and VH3, with humanized heavy chain variable domain amino acid sequences as depicted in SEQ ID NO's: 61, 62 and 63, respectively. Table 4 lists the amino acid sequences of framework regions in the three humanized heavy chain variable domains according to IMGT numbering.

TABLE 4

Amino acid sequences of the heavy chain framework regions in the three humanized heavy chain variable domains according to IMGT numbering

| Ab | FR | Amino acid sequence | SEQ ID NO |
|---|---|---|---|
| VH1 | 1 | EVQLLESGGGFVKPGGSLKLSCVVS | 40 |
| VH1 | 2 | MSWVRQTPEKRLVWVAT | 43 |
| VH1 | 3 | YYPDSVKGRFTISRDNVRNILYLQMSSLRSEDTAVYYC | 45 |
| VH1 | 4 | WGTGTTVTVSS | 48 |
| VH2 | 1 | EVQLVESGGGLVKPGGSLRLSCAAP | 41 |
| VH2 | 2 | MNWVRQAPGKGLEWVST | 44 |
| VH2 | 3 | YYPDSVKGRFTISRDNAANSLYLQMNSLRAEDTAVYYC | 46 |
| VH2 | 4 | WGQGTLVTVSS | 49 |
| VH3 | 1 | EVQLVESGGGLVQPGGSLRLSCAVS | 42 |
| VH3 | 2 | MNWVRQAPGKGLEWVST | 44 |
| VH3 | 3 | YYPDSVKGRFTISRDNSKNTLYLQMNSLRAEDTASYYC | 47 |
| VH3 | 4 | WGQGTLVTVSS | 49 |

For humanization of the light chain online databases of Human IgG sequences were searched for comparison to the murine VL domain using BLAST search algorithms, and candidate human variable domains selected from the top 200 BLAST results. These were reduced to three candidates based on a combination of framework homology, maintaining key framework residues and canonical loop structure, respectively ABI74066 (SEQ TD NO: 70), ABA26122 (SEQ TD NO: 71) and ABU90653 (SEQ ID NO: 72). With the CDRs of the murine anti-human CCR7 MAb 729 VH grafted into these acceptor frameworks they become the humanized variants VK1, VK2 and VK3, with humanized heavy chain variable domain amino acid sequences of SEQ ID NO: 64, 65 and 66, respectively. Table 5 lists the amino acid sequences of framework regions in the three humanized light chain variable domains according to IMGT numbering.

TABLE 5

Amino acid sequences of the light chain framework regions in the three humanized light chain variable domains according to IMGT numbering

| Ab | FR | Amino acid sequence | SEQ ID NO |
|---|---|---|---|
| VK1 | 1 | DIQMTQSPSSLSASVGDRVTITCRAS | 50 |
| VK1 | 2 | LNWYQQKPGKAPKRLIY | 52 |
| VK1 | 3 | NLDSGVPSRFSGSGSGTDFTLTISSLQPEDFATYYC | 55 |
| VK1 | 4 | FGQGTKVEIK | 58 |
| VK2 | 1 | EIVMTQSPSSLSASVGDRVTITCRAS | 51 |
| VK2 | 2 | LNWYQQKPGKAPKLLIY | 53 |
| VK2 | 3 | NLDSGVPSRFSGSGSGTDYTLTISSLQPEDFATYYC | 56 |
| VK2 | 4 | FGQGTKLEIK | 59 |
| VK3 | 1 | DIQMTQSPSSLSASVGDRVTITCRAS | 50 |
| VK3 | 2 | LAWLQQKPGKAPKSLIY | 54 |
| VK3 | 3 | NLDSGVPSKFSGSGSGTDFSLTISSLQPEDFATYYC | 57 |
| VK3 | 4 | FGQGTRLEIK | 60 |

The original VK3 variant contained an N-linked glycosylation motif (NXS/T, wherein X is any amino acid except proline). This N-linked glycosylation motif was removed by changing the asparagine residue at position 72 to a serine residue. The asparagine was mutated to a serine, which was the residue at this position in the murine VL. Some human antibodies also contain a serine at this position. Other than this N-linked glycosylation motif in the VK3 variant, no further N-linked glycosylation motifs were found present in the sequences of the other humanized variants.

4. Evaluation of Humanized Anti-CCR7 mAbs 4.1 Binding to Immunogen SYM1899

ELISA to evaluate binding of antibody 650 variants to immunogen SYM1899, a sulfated peptide derived from the N-terminus of human CCR7, (residues 19-49). SEQ ID NO: 76). 100 ng/well SYM1899 was immobilized onto 96 well Maxisorp plates in coating buffer. Coating buffer was removed and 200 µl/well of block solution (3% w/v semi skim milk powder, PBS) was added and agitated 2 hours room temperature. Plate was washed six times with PBS-T (0.001% v/v TWEEN 20 (Polysorbate 20). Antibody 650 variants were diluted to 1 ug/ml in PBS and a serial 1:1 dilution in PBS made to a concentration of 0.0078 µg/ml. 100 µl per well in triplicate of each antibody dilution was added to the plate in addition to a negative control of PBS and incubated 2 hours at room temperature with agitation. Plate was washed six times with PBS-T. 100 µl/well goat anti human HRP (Fc specific) (1:60,000 in PBS) was added and plates incubated for one hour agitated at room temperature. Plate was washed six times with PBS-T and once in PBS. 100 µl/well of TMB substrate solution was added and incubated at 37° C. for 10 minutes. 50 µl 1M HCl was added per well and the plate immediately read at 450 nm on a Biolise plate reader.

TABLE 6

Kd determination for antibody 650 variants
calculated using a 4 parameter logistics
curve fit.

| Antibody 650 variant | Kd (nM) |
|---|---|
| HC0 LC0 | 2.14 |
| HC1 LC1 | 1.78 |
| HC1 LC2 | 3.29 |
| HC1 LC3 | >100 |
| HC2 LC1 | 10.05 |
| HC2 LC2 | 8.33 |
| HC2 LC3 | >100 |
| HC3 LC1 | 4.404 |
| HC3 LC2 | 3.05 |
| HC3 LC3 | >100 |

Humanisation of mAb 650 was successful with a number of potential candidate variants identified. All three antibody 650 variants comprising the LC3 light chain variant did not bind well to SYM1899 and gave Kd's higher than 100.

HC1 LC1 yielded the best Kd of 1.78 and was the only construct which surprisingly bound to SYM1899 even better than chimeric HC0 LC0 with a Kd of 2.14.

4.2 Antibody 650 Variants 1-1, 2-1 and 3-1 Mediate ADCC in CLL Cells

Figure 5:
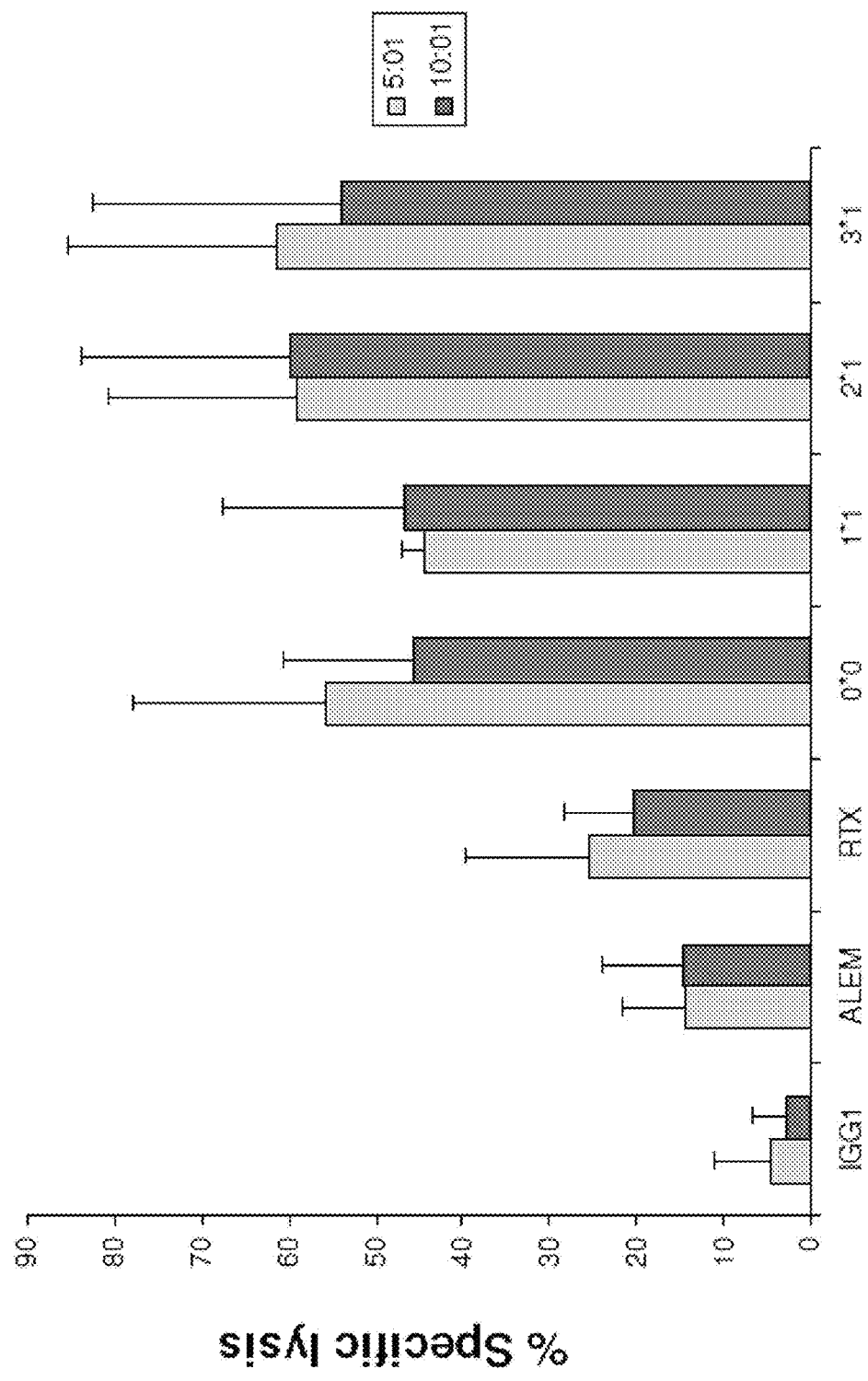
FIG. 5. Humanized anti-CCR7 mAbs (1*1=HC1 LC1, 2*1=HC2 LC1 and 3.1=HC3 LC1) and chimeric anti-human CCR7 mAb (Fab mouse/Fc human, 0*0=HC0 LC0) induced lysis of leukemic lymphocytes. Positive controls: mAbs Alemtuzumab (ALEM) and RITUXAN® (Rituximab) (RTX) and negative control: IGG1. The ADCC-assay (n=2) was executed with an Effector cells/Target cells (CLL cells) ratio 5:1 (light grey bars) and 10:1 (dark gray bars).

Three humanized anti-human CCR7 IgG1 mAbs comprising the same light chain variant (LC1, i.e. HeavyChain*LightChain: 1*1=HC1 LC1; 2*1=HC2 LC1; and 3.1=HC3 LC1) and the chimeric anti-human CCR7 mAb (Fab mouse/Fc human: 0*0=HC0 LC0) killed 50-60% of the malignant T-cells from chronic lymphocytic leukemia patients as determined by an Antibody Dependent Cell Cytotoxicity (ADCC) assay (n=2) (FIG. 5). Alemtuzumab (ALEM) and RITUXAN® (Rituximab) (RTX) were used as a positive controls and mAb IGG1 was used a negative control. The ADCC assay was performed as described by Somovilla-Crespo et al. (2013, J. of Hematol. & Oncol. 6:89).

4.3 Humanized Anti-CCR7 mAb 650 Inhibits CCR7 Receptor Internalization

Figure 6:
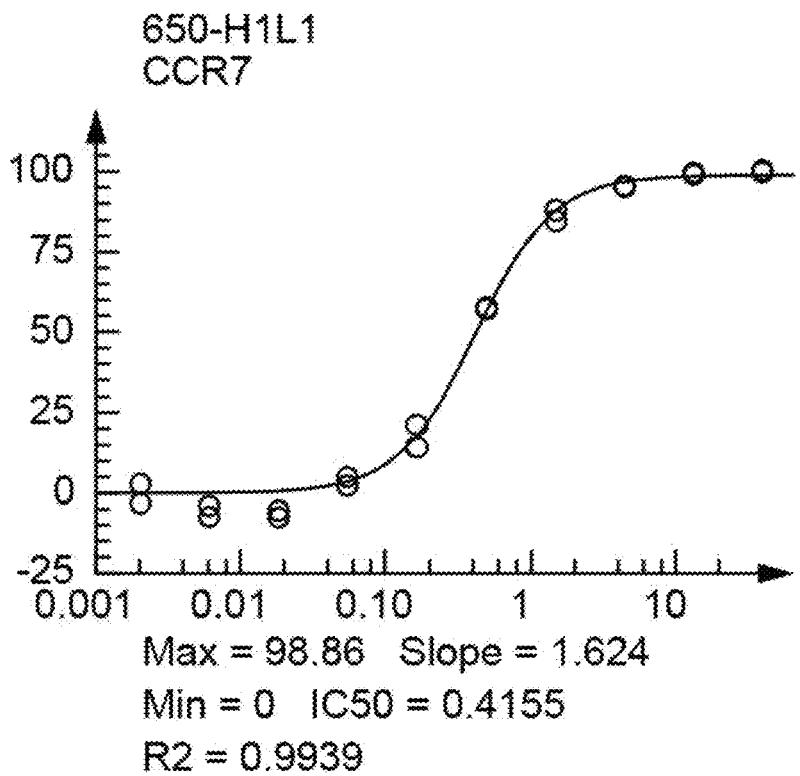
FIG. 6. Inhibition of CCL19 induced CCR7 receptor internalization by humanized anti-CCR7 mAb 650 as determined by an active internalization assay (PathHunter™, DiscoverX, Fremont, CA, USA). The concentration of mAb 650 (µg/ml) is plotted on the x-axis versus inhibition of CCL19 induced CCR7 internalization (% inhibition) on the y-axis.

The antagonistic activity of anti-CCR7 mAb 650-H1L1, is demonstrated by inhibition of the CCL19 induced CCR7 receptor internalization ($IC_{50}$ 0.4155 µg/ml=2.8 nM; tested range: 267-0.014 nM) (FIG. 6) as determined by an established active internalization assay (PathHunter™, DiscoverX, Fremont, CA, USA), essentially as described below.

Active Internalization Assay Design: GPCR Endocytosis

Using EFC technology, DiscoveRx has developed several methods to study receptor internalization. PathHunter® Activated GPCR Internalization Assays provide a quantitative measurement of arrestin-mediated GPCR internalization, allowing to monitor the movement of unlabelled, arrestin-bound GPCRs from the plasma membrane in live cells.

For antagonist determination, cells were pre-incubated with antagonist followed by agonist challenge at the EC80 concentration. Intermediate dilution of sample stocks was performed to generate 5× sample in assay buffer. 5 µL of 5× sample was added to cells and incubated at 37° C. or room temperature for 30 minutes. Vehicle concentration was 1%. 5 µL of 6×EC80 agonist in assay buffer was added to the cells and incubated at 37° C. or room temperature for 90 or 180 minutes (EA-Arrestin/EA-Endosome) or 37° C. for 16 hours (EA-Membrane).

Signal Detection

Assay signal was generated through a single addition of 12.5 or 15 µL (50% v/v) of PathHunter Detection reagent cocktail, followed by one hour incubation at room temperature. Microplates were read following signal generation with a PerkinElmer Envision™ instrument for chemiluminescent signal detection.

Data Analysis

Compound activity was analyzed using CBIS data analysis suite (ChemInnovation, CA). For the antagonist mode assay, percentage inhibition was calculated using the following formula: % Inhibition=100%×(1−(mean RLU of test sample−mean RLU of vehicle control)/(mean RLU of EC80 control−mean RLU of vehicle control)).

Figure 7:
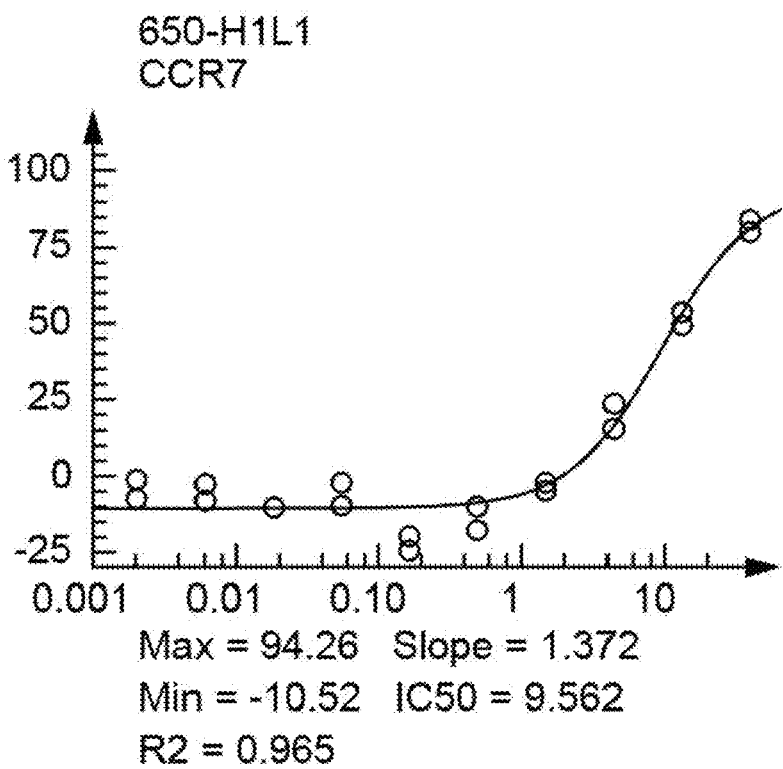
FIG. 7. Inhibition of CCL19 induced CCR7-dependent intracellular signalling of the β-arrestin pathway by humanized anti-CCR7 mAb 650 as determined by an established β-arrestin recruitment assay (PathHunter™, DiscoverX, Fremont, CA, USA). The concentration of mAb 650 (µg/ml) is plotted on the x-axis versus inhibition of CCL19 induced β-arrestin recruitment (% inhibition) on the y-axis.

4.3 Humanized Anti-CCR7 mAb 650 Inhibits CCR7-Dependent Intracellular Signalling of the β-Arrestin Pathway CCL19 induced intracellular signalling of CCR7 is effectively inhibited by mAb 650-H1L1, a humanized version of murine mAb 729, ($IC_{50}$ 9.5622 µg/ml=63.7 nM; tested range 267-0.014 nM) (FIG. 7) as determined by an established β-arrestin recruitment assay (PathHunter™, DiscoverX, Fremont, CA, USA), essentially as described below.

Arrestin Pathway

The PathHunter® β-Arrestin assay monitors the activation of a GPCR in a homogenous, non-imaging assay format using a technology developed by DiscoveRx called Enzyme Fragment Complementation (EFC) with β-galactosidase (β-Gal) as the functional reporter.

Assay Design

Antagonist Modulation Format: For antagonist determination, cells were pre-incubated with antagonist followed by agonist challenge at the EC80 concentration. Intermediate dilution of sample stocks was performed to generate 5× sample in assay buffer. 5 µL of 5× sample was added to cells and incubated at 37° C. or room temperature for 30 minutes. Vehicle concentration was 1%. 5 µL of 6×EC80 agonist in assay buffer was added to the cells and incubated at 37° C. or room temperature for 90 or 180 minutes.

Signal Detection

Assay signal was generated through a single addition of 12.5 or 15 µL (50% v/v) of PathHunter Detection reagent cocktail, followed by one hour incubation at room temperature. Microplates were read following signal generation with a PerkinElmer Envision™ instrument for chemiluminescent signal detection.

Data Analysis

Compound activity was analyzed using CBIS data analysis suite (ChemInnovation, CA). For the antagonist mode assay, percentage inhibition was calculated using the following formula: % Inhibition=100%×(1−(mean RLU of test sample−mean RLU of vehicle control)/(mean RLU of EC80 control−mean RLU of vehicle control)).

Figure 8:
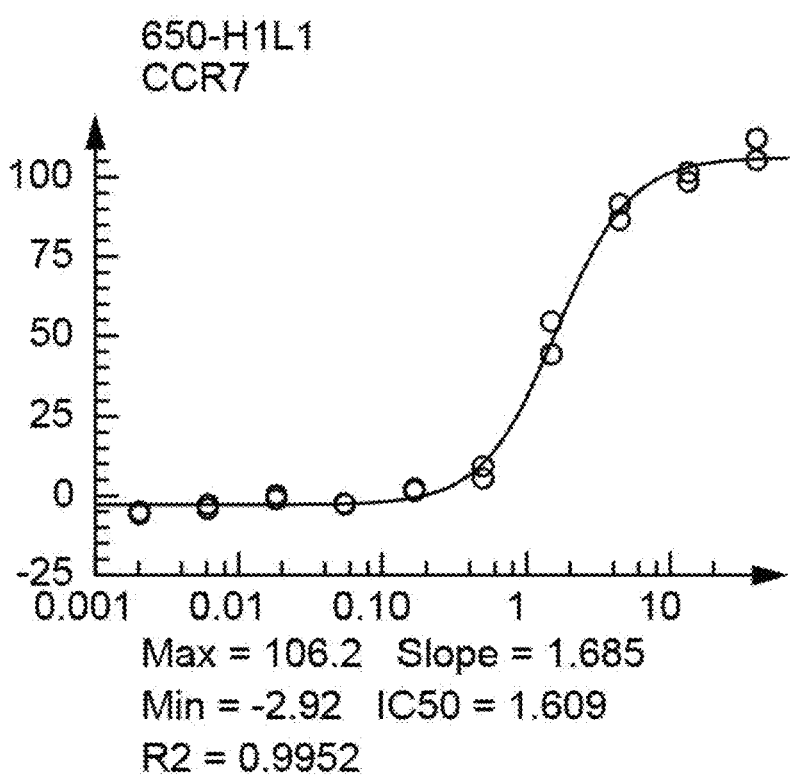
FIG. 8. Inhibition of CCL19 induced CCR7-dependent intracellular cAMP signalling by humanized anti-CCR7 mAb 650 as determined by an established cAMP Secondary Messenger Pathway assay (PathHunter™, DiscoverX, Fremont, CA, USA). The concentration of mAb 650 (µg/ml) is plotted on the x-axis versus inhibition of CCL19 induced CCR7 cAMP Secondary Messenger Pathway (% inhibition) on the y-axis.

4.4 Humanized Anti-CCR7 mAb 650 Inhibits CCR7-Dependent Intracellular cAMP Signalling mAb 650-H1L1 inhibits CCL19 induced CCR7-dependent intracellular cAMP signalling, ($IC_{50}$ 1.609 µg/ml=10.7 nM; tested range 267-0.014 nM) (FIG. 8) as determined by an established cAMP Secondary Messenger Pathway assay (PathHunter™, DiscoverX, Fremont, CA, USA), essentially as described below.

cAMP Secondary Messenger Pathway

DiscoveRx has developed a panel of cell lines stably expressing non-tagged GPCRs that endogenously signal through cAMP. Hit Hunter® cAMP assays monitor the activation of a GPCR via Gi and Gs secondary messenger signalling in a homogenous, non-imaging assay format using a technology developed by DiscoveRx called Enzyme Fragment Complementation (EFC) with β-galactosidase (β-Gal) as the functional endpoint.
Assay Design: GPCR cAMP Modulation
Inverse Agonist Format For inverse agonist determination, cells were preincubated with sample in the presence of EC20 forskolin. Media was aspirated from cells and replaced with 15 μL 2:1 HBSS/10 mM HEPES:cAMP XS+ Ab reagent. Intermediate dilution of sample stocks was performed to generate 4× sample in assay buffer containing 4×EC20 forskolin. 4.5 μL of 4× sample was added to cells and incubated at 37° C. or room temperature for 30 or 60 minutes. Final assay vehicle concentration was 1%.
Signal Detection After appropriate compound incubation, assay signal was generated through incubation with 20 μL cAMP XS+ ED/CL lysis cocktail for one hour followed by incubation with 20 μL cAMP XS+ EA reagent for three hours at room temperature. Microplates were read following signal generation with a PerkinElmer Envision™ instrument for chemiluminescent signal detection.
Data Analysis Compound activity was analyzed using CBIS data analysis suite (ChemInnovation, CA). For Gi inverse agonist mode assays, percentage activity is calculated using the following formula:

% Inverse Agonist Activity=100%×((mean RLU of test sample−mean RLU of EC20 forskolin)/(mean RLU of forskolin positive control−mean RLU of EC20 control)).

5. Allotype Switching and CDC-Enhanced Fc Mutants of the Humanized Anti-CCR7 Antibodies
5.1 Design of Allotype-Switched and CDC-Enhanced Mutants The original allotype of humanized anti-CCR7 mAb 650 variants 1-1, 2-1 and 3-1 (see 4.2. above for code) did not produce a sufficiently strong CDC effector function. The allotype of the three variants 1-1, 2-1 and 3-1 was therefore switched to human allotype G1m17,1 to give variants 11-17, 21-17, 31-17, each having a heavy chain constant region as depicted in SEQ ID NO: 79. To further enhance CDC effector function, the heavy chain constant regions of these three variants was further modified by introducing the E333A substitution (as described by Idusogie et al., 2000, J. Immunol. 164: 4178-4184), to give variants 11-AE, 21-AE, 31-AE each having a heavy chain constant region as depicted in SEQ ID NO: 80. In addition, a control antibody "11-x" was constructed by changing the HVR-H3 (CDR3) amino acid sequence in the heavy chain of the 11-17 antibody to the amino acid sequence of SEQ ID NO: 81, which completely abolished its ability to recognise and bind to CCR7. The antibodies were expressed transiently in CHO cells in 500 ml culture volumes, purified and used for further testing as described below, together with the chimeric HC0 LC0 antibody (see above), also referred to as "0-0".
5.2 Performance of the Allotype-Switched and CDC-Enhanced Mutants Humanized Anti-CCR7 Antibodies The performance of antibodies 11-17, 21-17, 31-17, 11-AE, 21-AE, 31-AE, 11-x and chimeric Ab 0-0 was next tested in a variety assays.

1. Binding of antibodies to membrane expressed CCR7 was determined by Fluorescence-activated cell sorting (FACS) by flow cytometry on three different chronic lymphocytic leukemia (CLL) samples and on three different T-cell Prolymphocytic leukaemia (TPLL) samples (data not shown). Appropriate controls (human isotype controls) were included to easily calculate the percentage of positive cells and/or the relative median fluorescence intensity (RMFI), obtained from the ratio MFI(sample)/MFI(control). On the CLL samples the antibodies 11-AE, 11-17, 31-17, 31-AE performed best and even outperformed the chimeric 0-0 antibody. On the TPLL samples the antibodies 11-AE and 11-17 performed best. The antibodies 11-AE, 11-17, 31-17, 31-AE showed similar FACS profiles on T-cells obtained from two healthy donors (HD), while they did not bind to neutrophils, monocytes or NK cells (data not shown).
2. The antibodies were tested for their ability to mediate complement-dependent cytotoxicity (CDC) on three different CLL samples and one TPLL sample (data not shown). The CDC assays were essentially performed as described by Cuesta-Mateos et al. (2015, supra). Antibodies 11-17, 11-AE and 31-AE showed the best response in mediating CDC in freshly isolated CLL cells of samples #1 and #3. Antibodies 11-17 and 11-AE showed a response in mediating CDC on CLL cells of sample #2. Antibodies 11-17, 11-AE, 21-AE and 31-AE showed a response in mediating CDC on TPLL cells of sample #1.

On the basis of the above results on the performance of the antibodies in FACS profile and mediation of CDC antibodies 11-AE, 11-17, 31-17 and 31-AE were selected for further testing.

3. Of the four selected antibodies, 11-AE and 11-17 showed the best CDC profile on a fourth CLL sample (data not shown).
4. The four selected antibodies were further tested for their ability to mediate ADCC. ADCC assay were performed as follows:
   A) Target cells: isolated PBMC or malignant cells derived from patients were incubated at 37° C. for 30 min with media alone (RPMI+0.1% BSA) or with media in the presence of the tested antibodies at a final concentration of 10 μg/ml. Depending on the sample used, an isotype control (IC) and/or anti-CD52 (alemtuzumab) and/or anti-CD20 (rituximab) and/or anti-CCR7 antibodies were tested. Unbound antibody was washed off twice by adding 2 ml of RPMI+0.1% BSA and spinning cells at 1800 rpm for 2 minutes.
   B) Effector cells: Human or mouse PBLs were obtained by Ficoll density gradient centrifugation. The proportion of NK cells and monocytes was determined by FACS as described above using antibodies directed against CD16-PE and CD14-APC.
   C) To discriminate target cells and effector cells, PBLs were labelled with calcein-UV Cell Tracker (Invivogen) according to the manufacturer's protocol. Briefly, 1 μL of 5 mM Cell Tracker solution was added to each mL of cell suspension in PBS (1×106 cells/mL) for a final working concentration of 5 μM. Sample was incubated for 20 minutes at 37° C., protected from light. Then, five times the original staining volume of culture medium was added to the cells and incubated for 5 minutes (this step removes any freed dye remaining in the solution) and cells were pelleted by centrifugation at 1800 rpm for 2 minutes.
   D) Target cells were plated in a 96-well round-bottom plate at 104 cells/well in RPMI+10% FBS. Then calcein-UV-labelled PBLs were used as effector cells (as effector of cell lysis) at different effector-to-target ratios (E:T). After 4 h of incubation, the target cells were stained with several specific markers and cell viability was determined by 7AAD staining. Each sample was analyzed by flow cytometry. The percentage of target cells killed by ADCC was determined by: % lysis=100×(ER−SR)/(MR−SR). ER, SR, and MR represent experimental, spontaneous and maximum cell death. Data were normalized to the media control.

All four selected antibodies outperformed alemtuzumab and rituximab in mediating ADCC using isolated PBLs on 2 different CLL samples (data not shown).

5. All four selected antibodies were able to mediate ADCC using isolated PBLs on an alemtuzumab-refractory CLL sample (data not shown).
6. Flow cytometry affinity profiles (FCAP) showed that all four selected antibodies have similar binding profiles on CLL and TPLL cells, although the antibodies with the 11 heavy chain combination have slightly higher affinities than the antibodies with the 31 heavy chain combination (data not shown).
7. In both CLL and TPLL samples all four selected antibodies block migration towards CCL19, however antibody 31-AE is slightly less effective blocking migration towards CCL21 (data not shown).

Table 7 presents an overview of the above results, wherein the individual allotype-switched and CDC-enhanced mutants humanized anti-CCR7 antibody variants are ranked according to their relative performance in the above assays. The 11-x did not show any binding to membrane expressed CCR7 as analysed by FACS, nor did it mediate CDC or ADCC.

TABLE 7

Overview and ranking of the relative performance of the allotype-switched and CDC-enhanced mutants humanized anti-CCR7 antibody variants in the assay as described in Example 5.

| Ab | FACS CLL #1 | FACS TPLL #1 | CDC CLL #1 | FACS CLL #2 | CDC CLL #2 | FACS TPLL #2 | CDC CLL #3 | FACS HD | FACS TPLL #3 | FACS CLL #3 | CDC CLL #3 |
|---|---|---|---|---|---|---|---|---|---|---|---|
| 11-17 | 6 | 5 | 5 | 5 | 0 | 6 | 5 | 6 | 5 | 5 | 5 |
| 21-17 | 2 | 2 | 2 | 1 | 0 | 2 | 1 | 1 | 1 | 1 | 1 |
| 31-17 | 4 | 4 | 1 | 3 | 0 | 4 | 2 | 3 | 3 | 3 | 2 |
| 11-AE | 5 | 6 | 6 | 6 | 0 | 5 | 6 | 5 | 6 | 6 | 6 |
| 21-AE | 1 | 1 | 3 | 2 | 0 | 1 | 3 | 2 | 2 | 2 | 3 |
| 31-AE | 3 | 3 | 4 | 4 | 0 | 3 | 4 | 4 | 4 | 4 | 4 |

| Ab | CDC TPLL | TW TPLL | FCAP TPLL | CDC CLL #4 | ADCC CLL #5 | ADCC CLL #6 | ADCC TPLL | TW CLL | FCAP CLL | Total score |
|---|---|---|---|---|---|---|---|---|---|---|
| 11-17 | 4 | 2 | 3 | 3 | 1 | 1 | 1 | 2 | 4 | 74 |
| 21-17 | 1 | 2 | | | | | | | | 17 |
| 31-17 | 2 | 2 | 1 | 1 | 1 | 2 | 1 | 2 | 2 | 43 |
| 11-AE | 6 | 1 | 4 | 4 | 1 | 1 | 2 | 2 | 3 | 81 |
| 21-AE | 3 | 2 | | | | | | | | 25 |
| 31-AE | 5 | 2 | 2 | 2 | 2 | 1 | 1 | 1 | 1 | 54 |

The invention claimed is:

1. A method for treating hepatic fibrosis, renal fibrosis, pulmonary fibrosis, skin fibrosis, cardiovascular fibrosis and/or gastrointestinal fibrosis, comprising administering a humanized anti- C-C chemokine receptor type 7 (anti-CCR7) antibody comprising the hypervariable regions HVR-H1, HVR-H2, HVR-H3, HVR-L1, HVR-L2 and HVR-L3, wherein:
   HVR-H1 comprises SEQ ID NO: 6;
   HVR-H2 H1 comprises SEQ ID NO: 13;
   HVR-H3 H1 comprises SEQ ID NO: 19;
   HVR-L1 H1 comprises SEQ ID NO: 27;
   HVR-L2 H1 comprises SEQ ID NO: 31; and
   HVR-L3 H1 comprises SEQ ID NO: 36,
   and wherein the antibody has at least one of:
   a) a minimal affinity for a synthetic antigen with the amino acid sequence of SEQ ID NO: 76, wherein the minimal affinity is defined by a $K_d$ that is not more than a 10× higher than the $K_d$ of a mouse anti-CCR7 antibody of which the amino acid sequence of the heavy chain variable domain is SEQ ID NO: 1 and of which the amino acid sequence of the light chain variable domain is SEQ ID NO: 2; and,
   b) an $IC_{50}$ of no more than 100 nM for inhibiting CCR7-dependent intracellular signalling and/or CCR7 receptor internalization, by at least one CCR7-ligand selected from CCL19 and CCL21.

2. The method according to claim 1, wherein the heavy chain variable domain of the antibody comprises 4 heavy chain framework regions, HFR1 to HFR4, and 3 hypervariable regions HVR-H1 to HVR-H3 that are operably linked in the order HFR1, HVR-H1, HFR2, HVR-H2, HFR3, HVR-H3 and HFR4, wherein the light chain variable domain of the antibody comprises 4 light chain framework regions, LFR1 to LFR4, and 3 hypervariable regions HVR-L1 to HVR-L3 that are operably linked in the order LFR1, HVR-L1, LFR2, HVR-L2, LFR3, HVR-L3 and LFR4, wherein the heavy chain framework regions HFR1 to HFR4 have the amino acid sequences of:
   i) SEQ ID NO's: 40, 43, 45 and 48, respectively;
   ii) SEQ ID NO's: 41, 44, 46 and 49, respectively; or,
   iii) SEQ ID NO's: 42, 44, 47 and 49, respectively,
   and wherein the light chain framework regions LFR1 to LFR4 have the amino acid sequences of:
   iv) SEQ ID NO's: 50, 52, 55 and 58, respectively; or,
   V) SEQ ID NO's: 51, 53, 56 and 59, respectively.

3. The method according to claim 1, wherein the heavy chain variable domain of the antibody comprises an amino acid sequence with at least 95% sequence identity to at least one of SEQ ID NO's: 61, 62 and 63, and wherein the light chain variable domain of the antibody comprises an amino acid sequence with at least 95% sequence identity to at least one of SEQ ID NO's: 64 and 65.

4. The method according to claim 3, wherein the heavy chain variable domain of the antibody comprises the amino acid sequence of SEQ ID NO: 61 and the light chain variable domain of the antibody comprises the amino acid sequence of SEQ ID NO: 64.

5. The method according to claim 1, wherein the heavy chain variable domain of the antibody comprises the amino acid sequence of SEQ ID NO: 61 and the light chain variable domain of the antibody comprises the amino acid sequence of SEQ ID NO: 64.

6. The method according to claim 1, wherein the antibody comprises a heavy chain constant region that is an IgG1, IgG2, IgG3 or IgG4 region.

7. The method according to claim 1, wherein the antibody comprises a functional Fc region possessing at least one effector function selected from the group consisting of: C1q binding, complement dependent cytotoxicity, Fc receptor binding, antibody-dependent cell-mediated cytotoxicity and phagocytosis.

8. The method according to claim 1, wherein the antibody comprises a heavy chain constant region of the allotype G1m17,1.

9. The method according to claim 8, wherein the heavy chain constant region comprises the amino acid sequence of SEQ ID NO: 80.

* * * * *

SEQUENCE LISTING

<160> NUMBER OF SEQ ID NOS: 81

<210> SEQ ID NO 1
<211> LENGTH: 125
<212> TYPE: PRT
<213> ORGANISM: Mus musculus

<400> SEQUENCE: 1

Glu Val Gln Leu Val Glu Ser Gly Gly Asp Leu Val Lys Pro Gly Gly
1               5                   10                  15

Ser Leu Lys Leu Ser Cys Val Val Pro Gly Leu Thr Phe Arg Asp Phe
            20                  25                  30

Ala Met Ser Trp Val Arg Gln Ile Pro Glu Lys Arg Leu Gln Trp Val
        35                  40                  45

Ala Thr Ile Ser Ser Gly Gly Phe Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ser Glu Asp Thr Ala Met Tyr Tyr Cys
                85                  90                  95

Val Arg Arg Ala Tyr Arg Tyr Asp Gly Thr Gly Asp Tyr Ser Ala Leu

```
            100                 105                 110
Asp Tyr Trp Gly Gln Gly Thr Ser Val Thr Val Ser Ser
        115                 120                 125

<210> SEQ ID NO 2
<211> LENGTH: 107
<212> TYPE: PRT
<213> ORGANISM: Mus musculus

<400> SEQUENCE: 2

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Pro Ser
            20                  25                  30

Leu Asn Trp Leu Gln Gln Gly Pro Asp Gly Thr Ile Lys Arg Leu Ile
        35                  40                  45

Tyr Ala Thr Ser Asn Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Val Asp Tyr Tyr Cys Leu Gln Phe Ala Ser Ser Pro Leu
                85                  90                  95

Thr Phe Gly Ala Gly Thr Lys Leu Glu Leu Lys
            100                 105

<210> SEQ ID NO 3
<211> LENGTH: 8
<212> TYPE: PRT
<213> ORGANISM: Mus musculus

<400> SEQUENCE: 3

Gly Phe Thr Phe Ser Asp Tyr Ala
1               5

<210> SEQ ID NO 4
<211> LENGTH: 8
<212> TYPE: PRT
<213> ORGANISM: Mus musculus

<400> SEQUENCE: 4

Gly Phe Ala Phe Ser Ser Tyr Ala
1               5

<210> SEQ ID NO 5
<211> LENGTH: 8
<212> TYPE: PRT
<213> ORGANISM: Mus musculus

<400> SEQUENCE: 5

Gly Phe Ala Phe Ser Asn Tyr Ala
1               5

<210> SEQ ID NO 6
<211> LENGTH: 8
<212> TYPE: PRT
<213> ORGANISM: Mus musculus

<400> SEQUENCE: 6

Gly Leu Thr Phe Arg Asp Phe Ala
1               5
```

```
<210> SEQ ID NO 7
<211> LENGTH: 8
<212> TYPE: PRT
<213> ORGANISM: Mus musculus

<400> SEQUENCE: 7

Gly Phe Pro Phe Ser Asn Tyr Ala
1               5

<210> SEQ ID NO 8
<211> LENGTH: 8
<212> TYPE: PRT
<213> ORGANISM: Mus musculus

<400> SEQUENCE: 8

Gly Phe Thr Phe Thr Asp Tyr Ala
1               5

<210> SEQ ID NO 9
<211> LENGTH: 8
<212> TYPE: PRT
<213> ORGANISM: Mus musculus

<400> SEQUENCE: 9

Gly Phe Thr Phe Ser Asn Tyr Ala
1               5

<210> SEQ ID NO 10
<211> LENGTH: 8
<212> TYPE: PRT
<213> ORGANISM: Mus musculus

<400> SEQUENCE: 10

Gly Phe Thr Phe Ser Ser Tyr Ala
1               5

<210> SEQ ID NO 11
<211> LENGTH: 8
<212> TYPE: PRT
<213> ORGANISM: Mus musculus

<400> SEQUENCE: 11

Ile Ser Asp Gly Gly Ser His Thr
1               5

<210> SEQ ID NO 12
<211> LENGTH: 8
<212> TYPE: PRT
<213> ORGANISM: Mus musculus

<400> SEQUENCE: 12

Ile Ser Asp Gly Gly Thr Tyr Pro
1               5

<210> SEQ ID NO 13
<211> LENGTH: 8
<212> TYPE: PRT
<213> ORGANISM: Mus musculus

<400> SEQUENCE: 13

Ile Ser Ser Gly Gly Phe Tyr Thr
1               5

<210> SEQ ID NO 14
<211> LENGTH: 8
```

```
<212> TYPE: PRT
<213> ORGANISM: Mus musculus

<400> SEQUENCE: 14

Ile Ser Ser Gly Gly Ser Tyr Thr
1               5

<210> SEQ ID NO 15
<211> LENGTH: 8
<212> TYPE: PRT
<213> ORGANISM: Mus musculus

<400> SEQUENCE: 15

Ile Ser Asp Arg Gly Ser Phe Thr
1               5

<210> SEQ ID NO 16
<211> LENGTH: 8
<212> TYPE: PRT
<213> ORGANISM: Mus musculus

<400> SEQUENCE: 16

Ile Ser Ser Gly Gly Ser His Thr
1               5

<210> SEQ ID NO 17
<211> LENGTH: 15
<212> TYPE: PRT
<213> ORGANISM: Mus musculus

<400> SEQUENCE: 17

Gly Arg Arg Ala Gly Arg Tyr Asp Glu Arg Asp Ala Met Asp Tyr
1               5                   10                  15

<210> SEQ ID NO 18
<211> LENGTH: 15
<212> TYPE: PRT
<213> ORGANISM: Mus musculus

<400> SEQUENCE: 18

Thr Arg Arg Ala Tyr Arg Tyr Asp Val Lys Asn Ser Met Asp Tyr
1               5                   10                  15

<210> SEQ ID NO 19
<211> LENGTH: 18
<212> TYPE: PRT
<213> ORGANISM: Mus musculus

<400> SEQUENCE: 19

Val Arg Arg Ala Tyr Arg Tyr Asp Gly Thr Gly Asp Tyr Ser Ala Leu
1               5                   10                  15

Asp Tyr

<210> SEQ ID NO 20
<211> LENGTH: 14
<212> TYPE: PRT
<213> ORGANISM: Mus musculus

<400> SEQUENCE: 20

Ala Arg Arg Glu Tyr Arg Tyr Ala Glu Asn Ala Met Asp Tyr
1               5                   10

<210> SEQ ID NO 21
<211> LENGTH: 15
```

```
<212> TYPE: PRT
<213> ORGANISM: Mus musculus

<400> SEQUENCE: 21

Thr Arg Arg Ala Tyr Arg Tyr Asp Gly Asp Asn Ala Met Asp Tyr
1               5                   10                  15

<210> SEQ ID NO 22
<211> LENGTH: 15
<212> TYPE: PRT
<213> ORGANISM: Mus musculus

<400> SEQUENCE: 22

Ala Arg Arg Ala Tyr Arg Tyr Asp Glu Asp Ser Ala Met Asp Ser
1               5                   10                  15

<210> SEQ ID NO 23
<211> LENGTH: 13
<212> TYPE: PRT
<213> ORGANISM: Mus musculus

<400> SEQUENCE: 23

Ala Arg Ala Thr Thr Val Val Gly Thr Asp Phe Asp Tyr
1               5                   10

<210> SEQ ID NO 24
<211> LENGTH: 7
<212> TYPE: PRT
<213> ORGANISM: Mus musculus

<400> SEQUENCE: 24

Ser Ser Val Ser Ser Ser Tyr
1               5

<210> SEQ ID NO 25
<211> LENGTH: 6
<212> TYPE: PRT
<213> ORGANISM: Mus musculus

<400> SEQUENCE: 25

Gln Asp Ile Gly Asp Asn
1               5

<210> SEQ ID NO 26
<211> LENGTH: 6
<212> TYPE: PRT
<213> ORGANISM: Mus musculus

<400> SEQUENCE: 26

Gln Asp Ile Gly Asn Asn
1               5

<210> SEQ ID NO 27
<211> LENGTH: 6
<212> TYPE: PRT
<213> ORGANISM: Mus musculus

<400> SEQUENCE: 27

Gln Asp Ile Gly Pro Ser
1               5

<210> SEQ ID NO 28
<211> LENGTH: 6
<212> TYPE: PRT
<213> ORGANISM: Mus musculus
```

```
<400> SEQUENCE: 28

Gln Asp Ile Gly Gly Ser
1               5

<210> SEQ ID NO 29
<211> LENGTH: 11
<212> TYPE: PRT
<213> ORGANISM: Mus musculus

<400> SEQUENCE: 29

Gln Ser Leu Leu Asp Ser Asp Gly Lys Thr Tyr
1               5                   10

<210> SEQ ID NO 30
<211> LENGTH: 6
<212> TYPE: PRT
<213> ORGANISM: Mus musculus

<400> SEQUENCE: 30

Gln Asp Ile Gly Ser Ser
1               5

<210> SEQ ID NO 31
<211> LENGTH: 3
<212> TYPE: PRT
<213> ORGANISM: Mus musculus

<400> SEQUENCE: 31

Ala Thr Ser
1

<210> SEQ ID NO 32
<211> LENGTH: 3
<212> TYPE: PRT
<213> ORGANISM: Mus musculus

<400> SEQUENCE: 32

Ser Ile Ser
1

<210> SEQ ID NO 33
<211> LENGTH: 3
<212> TYPE: PRT
<213> ORGANISM: Mus musculus

<400> SEQUENCE: 33

Leu Val Ser
1

<210> SEQ ID NO 34
<211> LENGTH: 9
<212> TYPE: PRT
<213> ORGANISM: Mus musculus

<400> SEQUENCE: 34

Gln Gln Trp Ser Ser Asn Pro Pro Thr
1               5

<210> SEQ ID NO 35
<211> LENGTH: 9
<212> TYPE: PRT
<213> ORGANISM: Mus musculus

<400> SEQUENCE: 35
```

```
Leu Gln Tyr Ala Ser Ser Pro Leu Thr
1               5

<210> SEQ ID NO 36
<211> LENGTH: 9
<212> TYPE: PRT
<213> ORGANISM: Mus musculus

<400> SEQUENCE: 36

Leu Gln Phe Ala Ser Ser Pro Leu Thr
1               5

<210> SEQ ID NO 37
<211> LENGTH: 9
<212> TYPE: PRT
<213> ORGANISM: Mus musculus

<400> SEQUENCE: 37

Leu Gln Tyr Ala Asn Ser Pro Leu Thr
1               5

<210> SEQ ID NO 38
<211> LENGTH: 9
<212> TYPE: PRT
<213> ORGANISM: Mus musculus

<400> SEQUENCE: 38

Trp Gln Gly Thr His Phe Pro Gln Thr
1               5

<210> SEQ ID NO 39
<211> LENGTH: 9
<212> TYPE: PRT
<213> ORGANISM: Mus musculus

<400> SEQUENCE: 39

Leu Gln Tyr Ala Ser Ser Pro Pro Thr
1               5

<210> SEQ ID NO 40
<211> LENGTH: 25
<212> TYPE: PRT
<213> ORGANISM: Homo sapiens

<400> SEQUENCE: 40

Glu Val Gln Leu Leu Glu Ser Gly Gly Gly Phe Val Lys Pro Gly Gly
1               5                   10                  15

Ser Leu Lys Leu Ser Cys Val Val Ser
            20                  25

<210> SEQ ID NO 41
<211> LENGTH: 25
<212> TYPE: PRT
<213> ORGANISM: Homo sapiens

<400> SEQUENCE: 41

Glu Val Gln Leu Val Glu Ser Gly Gly Gly Leu Val Lys Pro Gly Gly
1               5                   10                  15

Ser Leu Arg Leu Ser Cys Ala Ala Pro
            20                  25

<210> SEQ ID NO 42
<211> LENGTH: 25
```

```
<212> TYPE: PRT
<213> ORGANISM: Homo sapiens

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Val Ser
            20                  25

<210> SEQ ID NO 43
<211> LENGTH: 17
<212> TYPE: PRT
<213> ORGANISM: Homo sapiens

<400> SEQUENCE: 43

Met Ser Trp Val Arg Gln Thr Pro Glu Lys Arg Leu Val Trp Val Ala
1               5                   10                  15

Thr

<210> SEQ ID NO 44
<211> LENGTH: 17
<212> TYPE: PRT
<213> ORGANISM: Homo sapiens

<400> SEQUENCE: 44

Met Ser Trp Val Arg Gln Ala Pro Gly Lys Gly Leu Glu Trp Val Ser
1               5                   10                  15

Thr

<210> SEQ ID NO 45
<211> LENGTH: 38
<212> TYPE: PRT
<213> ORGANISM: Homo sapiens

<400> SEQUENCE: 45

Tyr Tyr Pro Asp Ser Val Lys Gly Arg Phe Thr Ile Ser Arg Asp Asn
1               5                   10                  15

Val Arg Asn Ile Leu Tyr Leu Gln Met Ser Ser Leu Arg Ser Glu Asp
            20                  25                  30

Thr Ala Val Tyr Tyr Cys
        35

<210> SEQ ID NO 46
<211> LENGTH: 38
<212> TYPE: PRT
<213> ORGANISM: Homo sapiens

<400> SEQUENCE: 46

Tyr Tyr Pro Asp Ser Val Lys Gly Arg Phe Thr Ile Ser Arg Asp Asn
1               5                   10                  15

Ala Ala Asn Ser Leu Tyr Leu Gln Met Asn Ser Leu Arg Ala Glu Asp
            20                  25                  30

Thr Ala Val Tyr Tyr Cys
        35

<210> SEQ ID NO 47
<211> LENGTH: 38
<212> TYPE: PRT
<213> ORGANISM: Homo sapiens

<400> SEQUENCE: 47
```

Tyr Tyr Pro Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Ser Tyr Tyr Cys
            35

<210> SEQ ID NO 48
<211> LENGTH: 11
<212> TYPE: PRT
<213> ORGANISM: Homo sapiens

<400> SEQUENCE: 48

Trp Gly Thr Gly Thr Thr Val Thr Val Ser Ser
1               5                   10

<210> SEQ ID NO 49
<211> LENGTH: 11
<212> TYPE: PRT
<213> ORGANISM: Homo sapiens

<400> SEQUENCE: 49

Trp Gly Gln Gly Thr Leu Val Thr Val Ser Ser
1               5                   10

<210> SEQ ID NO 50
<211> LENGTH: 26
<212> TYPE: PRT
<213> ORGANISM: Homo sapiens

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser
            20                  25

<210> SEQ ID NO 51
<211> LENGTH: 26
<212> TYPE: PRT
<213> ORGANISM: Homo sapiens

<400> SEQUENCE: 51

Glu Ile Val Met Thr Gln Ser Pro Ser Ser Leu Ser Ala Ser Val Gly
1               5                   10                  15

Asp Arg Val Thr Ile Thr Cys Arg Ala Ser
            20                  25

<210> SEQ ID NO 52
<211> LENGTH: 17
<212> TYPE: PRT
<213> ORGANISM: Homo sapiens

<400> SEQUENCE: 52

Leu Asn Trp Tyr Gln Gln Lys Pro Gly Lys Ala Pro Lys Arg Leu Ile
1               5                   10                  15

Tyr

<210> SEQ ID NO 53
<211> LENGTH: 17
<212> TYPE: PRT
<213> ORGANISM: Homo sapiens

<400> SEQUENCE: 53

Leu Asn Trp Tyr Gln Gln Lys Pro Gly Lys Ala Pro Lys Leu Leu Ile
1               5                   10                  15

Tyr

<210> SEQ ID NO 54
<211> LENGTH: 17
<212> TYPE: PRT
<213> ORGANISM: Homo sapiens

<400> SEQUENCE: 54

Leu Asn Trp Leu Gln Gln Lys Pro Gly Lys Ala Pro Lys Ser Leu Ile
1               5                   10                  15

Tyr

<210> SEQ ID NO 55
<211> LENGTH: 36
<212> TYPE: PRT
<213> ORGANISM: Homo sapiens

<400> SEQUENCE: 55

Asn Leu Asp Ser Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35

<210> SEQ ID NO 56
<211> LENGTH: 36
<212> TYPE: PRT
<213> ORGANISM: Homo sapiens

<400> SEQUENCE: 56

Asn Leu Asp Ser Gly Val Pro Ser Arg Phe Ser Gly Ser Gly Ser Gly
1               5                   10                  15

Thr Asp Tyr Thr Leu Thr Ile Ser Ser Leu Gln Pro Glu Asp Phe Ala
            20                  25                  30

Thr Tyr Tyr Cys
        35

<210> SEQ ID NO 57
<211> LENGTH: 36
<212> TYPE: PRT
<213> ORGANISM: Homo sapiens

<400> SEQUENCE: 57

Asn Leu Asp Ser Gly Val Pro Ser Lys Phe Ser Gly Ser Gly Ser Gly
1               5                   10                  15

Thr Asp Phe Ser Leu Thr Ile Ser Ser Leu Gln Pro Glu Asp Phe Ala
            20                  25                  30

Thr Tyr Tyr Cys
        35

<210> SEQ ID NO 58
<211> LENGTH: 10
<212> TYPE: PRT
<213> ORGANISM: Homo sapiens

<400> SEQUENCE: 58

Phe Gly Gln Gly Thr Lys Val Glu Ile Lys

<210> SEQ ID NO 59
<211> LENGTH: 10
<212> TYPE: PRT
<213> ORGANISM: Homo sapiens

<400> SEQUENCE: 59

Phe Gly Gln Gly Thr Lys Leu Glu Ile Lys
1               5                   10

<210> SEQ ID NO 60
<211> LENGTH: 10
<212> TYPE: PRT
<213> ORGANISM: Homo sapiens

<400> SEQUENCE: 60

Phe Gly Gln Gly Thr Arg Leu Glu Ile Lys
1               5                   10

<210> SEQ ID NO 61
<211> LENGTH: 125
<212> TYPE: PRT
<213> ORGANISM: Artificial
<220> FEATURE:
<223> OTHER INFORMATION: Humanized VH1 domain

<400> SEQUENCE: 61

Glu Val Gln Leu Leu Glu Ser Gly Gly Gly Phe Val Lys Pro Gly Gly
1               5                   10                  15

Ser Leu Lys Leu Ser Cys Val Val Ser Gly Leu Thr Phe Arg Asp Phe
                20                  25                  30

Ala Met Ser Trp Val Arg Gln Thr Pro Glu Lys Arg Leu Val Trp Val
            35                  40                  45

Ala Thr Ile Ser Ser Gly Gly Phe Tyr Thr Tyr Tyr Pro Asp Ser Val
        50                  55                  60

Lys Gly Arg Phe Thr Ile Ser Arg Asp Asn Val Arg Asn Ile Leu Tyr
65                  70                  75                  80

Leu Gln Met Ser Ser Leu Arg Ser Glu Asp Thr Ala Val Tyr Tyr Cys
                85                  90                  95

Val Arg Arg Ala Tyr Arg Tyr Asp Gly Thr Gly Asp Tyr Ser Ala Leu
            100                 105                 110

Asp Tyr Trp Gly Thr Gly Thr Thr Val Thr Val Ser Ser
        115                 120                 125

<210> SEQ ID NO 62
<211> LENGTH: 125
<212> TYPE: PRT
<213> ORGANISM: Artificial
<220> FEATURE:
<223> OTHER INFORMATION: Humanized VH2 domain

<400> SEQUENCE: 62

Glu Val Gln Leu Val Glu Ser Gly Gly Gly Leu Val Lys Pro Gly Gly
1               5                   10                  15

Ser Leu Arg Leu Ser Cys Ala Ala Pro Gly Leu Thr Phe Arg Asp Phe
                20                  25                  30

Ala Met Ser Trp Val Arg Gln Ala Pro Gly Lys Gly Leu Glu Trp Val
            35                  40                  45

Ser Thr Ile Ser Ser Gly Gly Phe Tyr Thr Tyr Tyr Pro Asp Ser Val
        50                  55                  60

```
Lys Gly Arg Phe Thr Ile Ser Arg Asp Asn Ala Ala Asn Ser Leu Tyr
 65                  70                  75                  80

Leu Gln Met Asn Ser Leu Arg Ala Glu Asp Thr Ala Val Tyr Tyr Cys
                 85                  90                  95

Val Arg Arg Ala Tyr Arg Tyr Asp Gly Thr Gly Asp Tyr Ser Ala Leu
            100                 105                 110

Asp Tyr Trp Gly Gln Gly Thr Leu Val Thr Val Ser Ser
        115                 120                 125

<210> SEQ ID NO 63
<211> LENGTH: 125
<212> TYPE: PRT
<213> ORGANISM: Artificial
<220> FEATURE:
<223> OTHER INFORMATION: Humanized VH3 domain

<400> SEQUENCE: 63

Glu Val Gln Leu Val Glu Ser Gly Gly Leu Val Gln Pro Gly Gly
1               5                   10                  15

Ser Leu Arg Leu Ser Cys Ala Val Ser Gly Leu Thr Phe Arg Asp Phe
            20                  25                  30

Ala Met Ser Trp Val Arg Gln Ala Pro Gly Lys Gly Leu Glu Trp Val
        35                  40                  45

Ser Thr Ile Ser Ser Gly Gly Phe Tyr Thr Tyr Tyr Pro Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Ser Tyr Tyr Cys
                 85                  90                  95

Val Arg Arg Ala Tyr Arg Tyr Asp Gly Thr Gly Asp Tyr Ser Ala Leu
            100                 105                 110

Asp Tyr Trp Gly Gln Gly Thr Leu Val Thr Val Ser Ser
        115                 120                 125

<210> SEQ ID NO 64
<211> LENGTH: 107
<212> TYPE: PRT
<213> ORGANISM: Artificial
<220> FEATURE:
<223> OTHER INFORMATION: Humanized VK1 domain

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Pro Ser
            20                  25                  30

Leu Asn Trp Tyr Gln Gln Lys Pro Gly Lys Ala Pro Lys Arg Leu Ile
        35                  40                  45

Tyr Ala Thr Ser Asn Leu Asp Ser Gly Val Pro Ser Arg Phe Ser Gly
    50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Phe Ala Ser Ser Pro Leu
                 85                  90                  95

Thr Phe Gly Gln Gly Thr Lys Val Glu Ile Lys
            100                 105
```

```
<210> SEQ ID NO 65
<211> LENGTH: 107
<212> TYPE: PRT
<213> ORGANISM: Artificial
<220> FEATURE:
<223> OTHER INFORMATION: Humanized VK2 domain

<400> SEQUENCE: 65

Glu Ile Val Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Pro Ser
            20                  25                  30

Leu Asn Trp Tyr Gln Gln Lys Pro Gly Lys Ala Pro Lys Leu Leu Ile
        35                  40                  45

Tyr Ala Thr Ser Asn Leu Asp Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Phe Ala Ser Ser Pro Leu
                85                  90                  95

Thr Phe Gly Gln Gly Thr Lys Leu Glu Ile Lys
            100                 105

<210> SEQ ID NO 66
<211> LENGTH: 107
<212> TYPE: PRT
<213> ORGANISM: Artificial
<220> FEATURE:
<223> OTHER INFORMATION: Humanized VK3 domain

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Pro Ser
            20                  25                  30

Leu Asn Trp Leu Gln Gln Lys Pro Gly Lys Ala Pro Lys Ser Leu Ile
        35                  40                  45

Tyr Ala Thr Ser Asn Leu Asp Ser Gly Val Pro Ser Lys Phe Ser Gly
50                  55                  60

Ser Gly Ser Gly Thr Asp Phe Ser Leu Thr Ile Ser Ser Leu Gln Pro
65                  70                  75                  80

Glu Asp Phe Ala Thr Tyr Tyr Cys Leu Gln Phe Ala Ser Ser Pro Leu
                85                  90                  95

Thr Phe Gly Gln Gly Thr Arg Leu Glu Ile Lys
            100                 105

<210> SEQ ID NO 67
<211> LENGTH: 118
<212> TYPE: PRT
<213> ORGANISM: Homo sapiens

<400> SEQUENCE: 67

Glu Val Gln Leu Leu Glu Ser Gly Gly Gly Phe Val Lys Pro Gly Gly
1               5                   10                  15

Ser Leu Lys Leu Ser Cys Val Val Ser Gly Phe Thr Phe Ser Ser Tyr
            20                  25                  30

Ala Met Ser Trp Val Arg Gln Thr Pro Glu Lys Arg Leu Val Trp Val
        35                  40                  45

Ala Ser Ile Ser Ser Gly Asn Ile Ile Tyr Tyr Pro Asp Asn Val Lys
```

-continued

```
                50                  55                  60
Gly Arg Phe Thr Ile Ser Arg Asp Asn Val Arg Asn Ile Leu Tyr Leu
 65                  70                  75                  80

Gln Met Ser Ser Leu Arg Ser Glu Asp Thr Ala Val Tyr Tyr Cys Ala
                 85                  90                  95

Arg Gly Arg Ser Thr Tyr Gly Gly Phe Asp His Trp Gly Thr Gly Thr
            100                 105                 110

Thr Val Thr Val Ser Ser
            115
```

<210> SEQ ID NO 68
<211> LENGTH: 125
<212> TYPE: PRT
<213> ORGANISM: Homo sapiens

<400> SEQUENCE: 68

```
Glu Val Gln Leu Val Glu Ser Gly Gly Gly Leu Val Lys Pro Gly Gly
 1               5                  10                  15

Ser Leu Arg Leu Ser Cys Ala Ala Pro Gly Phe Thr Phe Ser Ser Tyr
                20                  25                  30

Ser Met Asn Trp Val Arg Gln Ala Pro Gly Lys Gly Leu Glu Trp Val
             35                  40                  45

Ser Ser Ile Ser Ser Ser Ser Tyr Met His Tyr Ala Asp Ser Val
 50                  55                  60

Lys Gly Arg Phe Thr Ile Ser Arg Asp Asn Ala Ala Asn Ser Leu Tyr
 65                  70                  75                  80

Leu Gln Met Asn Ser Leu Arg Ala Glu Asp Thr Ala Val Tyr Tyr Cys
                 85                  90                  95

Ala Ile Ala Asn Arg Gly Tyr Ser Tyr Asp Thr Leu Pro Ser Phe Val
            100                 105                 110

Asp Tyr Trp Gly Gln Gly Thr Leu Val Thr Val Ser Ser
            115                 120                 125
```

<210> SEQ ID NO 69
<211> LENGTH: 123
<212> TYPE: PRT
<213> ORGANISM: Homo sapiens

<400> SEQUENCE: 69

```
Glu Val Gln Leu Val Glu Ser Gly Gly Gly Leu Val Gln Pro Gly Gly
 1               5                  10                  15

Ser Leu Arg Leu Ser Cys Ala Val Ser Gly Phe Thr Phe Ser Ser Tyr
                20                  25                  30

Ala Met Asn Trp Val Arg Gln Ala Pro Gly Lys Gly Leu Glu Trp Val
             35                  40                  45

Ser Ala Ile Ser Gly Ser Ala Asp Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Ser Tyr Tyr Cys
                 85                  90                  95

Ala Lys Asp His Tyr Thr Asp Ser Ser Gly Trp Tyr Glu Leu Asp Tyr
            100                 105                 110

Trp Gly Gln Gly Thr Leu Val Thr Val Ser Ser
            115                 120
```

<210> SEQ ID NO 70
<211> LENGTH: 107
<212> TYPE: PRT
<213> ORGANISM: Homo sapiens

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ala
                85                  90                  95

Thr Phe Gly Gln Gly Thr Lys Val Glu Ile Lys
            100                 105

<210> SEQ ID NO 71
<211> LENGTH: 107
<212> TYPE: PRT
<213> ORGANISM: Homo sapiens

<400> SEQUENCE: 71

Glu Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Leu Glu Ile Lys
            100                 105

<210> SEQ ID NO 72
<211> LENGTH: 107
<212> TYPE: PRT
<213> ORGANISM: Homo sapiens

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Arg Asn Tyr
            20                  25                  30

Leu Ala Trp Leu Gln Gln Lys Pro Gly Lys Ala Pro Lys Ser Leu Ile
        35                  40                  45

Tyr Ala Ala Ser Ser Leu Gln Ser Gly Val Pro Ser Lys Phe Ser Gly
50                  55                  60

Ser Gly Ser Gly Thr Asp Phe Asn Leu Thr Ile Ser Ser Leu Gln Pro
65                  70                  75                  80

```
Glu Asp Phe Ala Thr Tyr Tyr Cys Gln Gln Tyr Thr Asn Tyr Pro Ile
                85                  90                  95

Thr Phe Gly Gln Gly Thr Arg Leu Glu Ile Lys
            100                 105

<210> SEQ ID NO 73
<211> LENGTH: 98
<212> TYPE: PRT
<213> ORGANISM: Homo sapiens

<400> SEQUENCE: 73

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
            35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 74
<211> LENGTH: 95
<212> TYPE: PRT
<213> ORGANISM: Homo sapiens

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 75
<211> LENGTH: 378
<212> TYPE: PRT
<213> ORGANISM: Homo sapiens

<400> SEQUENCE: 75

Met Asp Leu Gly Lys Pro Met Lys Ser Val Leu Val Val Ala Leu Leu
1               5                   10                  15

Val Ile Phe Gln Val Cys Leu Cys Gln Asp Glu Val Thr Asp Asp Tyr
                20                  25                  30

Ile Gly Asp Asn Thr Thr Val Asp Tyr Thr Leu Phe Glu Ser Leu Cys
            35                  40                  45

Ser Lys Lys Asp Val Arg Asn Phe Lys Ala Trp Phe Leu Pro Ile Met
```

```
                50                  55                  60
Tyr Ser Ile Ile Cys Phe Val Gly Leu Leu Gly Asn Gly Leu Val Val
 65                  70                  75                  80

Leu Thr Tyr Ile Tyr Phe Lys Arg Leu Lys Thr Met Thr Asp Thr Tyr
                 85                  90                  95

Leu Leu Asn Leu Ala Val Ala Asp Ile Leu Phe Leu Leu Thr Leu Pro
                100                 105                 110

Phe Trp Ala Tyr Ser Ala Ala Lys Ser Trp Val Phe Gly Val His Phe
            115                 120                 125

Cys Lys Leu Ile Phe Ala Ile Tyr Lys Met Ser Phe Phe Ser Gly Met
130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                165                 170                 175

Leu Ser Cys Val Gly Ile Trp Ile Leu Ala Thr Val Leu Ser Ile Pro
            180                 185                 190

Glu Leu Leu Tyr Ser Asp Leu Gln Arg Ser Ser Ser Glu Gln Ala Met
        195                 200                 205

Arg Cys Ser Leu Ile Thr Glu His Val Glu Ala Phe Ile Thr Ile Gln
210                 215                 220

Val Ala Gln Met Val Ile Gly Phe Leu Val Pro Leu Leu Ala Met Ser
225                 230                 235                 240

Phe Cys Tyr Leu Val Ile Ile Arg Thr Leu Leu Gln Ala Arg Asn Phe
                245                 250                 255

Glu Arg Asn Lys Ala Ile Lys Val Ile Ile Ala Val Val Val Val Phe
            260                 265                 270

Ile Val Phe Gln Leu Pro Tyr Asn Gly Val Val Leu Ala Gln Thr Val
        275                 280                 285

Ala Asn Phe Asn Ile Thr Ser Ser Thr Cys Glu Leu Ser Lys Gln Leu
290                 295                 300

Asn Ile Ala Tyr Asp Val Thr Tyr Ser Leu Ala Cys Val Arg Cys Cys
305                 310                 315                 320

Val Asn Pro Phe Leu Tyr Ala Phe Ile Gly Val Lys Phe Arg Asn Asp
                325                 330                 335

Leu Phe Lys Leu Phe Lys Asp Leu Gly Cys Leu Ser Gln Glu Gln Leu
            340                 345                 350

Arg Gln Trp Ser Ser Cys Arg His Ile Arg Arg Ser Ser Met Ser Val
        355                 360                 365

Glu Ala Glu Thr Thr Thr Thr Phe Ser Pro
370                 375

<210> SEQ ID NO 76
<211> LENGTH: 32
<212> TYPE: PRT
<213> ORGANISM: Artificial
<220> FEATURE:
<223> OTHER INFORMATION: SYM1899: synthetic sulfated peptide
      corresponding to amino acids 19-49 of human CCR7
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (8)..(8)
<223> OTHER INFORMATION: SULFATATION
<220> FEATURE:
```

```
<221> NAME/KEY: MOD_RES
<222> LOCATION: (17)..(17)
<223> OTHER INFORMATION: SULFATATION

<400> SEQUENCE: 76

Glu Asp Glu Val Thr Asp Asp Tyr Ile Gly Asp Asn Thr Thr Val Asp
1               5                   10                  15

Tyr Thr Leu Phe Glu Ser Leu Cys Ser Lys Lys Asp Val Arg Asn Lys
                20                  25                  30

<210> SEQ ID NO 77
<211> LENGTH: 19
<212> TYPE: PRT
<213> ORGANISM: Artificial
<220> FEATURE:
<223> OTHER INFORMATION: heavy chain signal peptide

<400> SEQUENCE: 77

Met Gly Trp Thr Leu Val Phe Leu Phe Leu Leu Ser Val Thr Ala Gly
1               5                   10                  15

Val His Ser

<210> SEQ ID NO 78
<211> LENGTH: 20
<212> TYPE: PRT
<213> ORGANISM: Artificial
<220> FEATURE:
<223> OTHER INFORMATION: light chain signal peptide

<400> SEQUENCE: 78

Met Val Ser Ser Ala Gln Phe Leu Gly Leu Leu Leu Leu Cys Phe Gln
1               5                   10                  15

Gly Thr Arg Cys
            20

<210> SEQ ID NO 79
<211> LENGTH: 330
<212> TYPE: PRT
<213> ORGANISM: Homo sapiens

<400> SEQUENCE: 79

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
```

```
            145                 150                 155                 160
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 80
<211> LENGTH: 330
<212> TYPE: PRT
<213> ORGANISM: Artificial
<220> FEATURE:
<223> OTHER INFORMATION: synthetic heavy chain constant region of the
      human allotype G1m (17,1) with a E333A substitution

<400> SEQUENCE: 80

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200             205

Lys Ala Leu Pro Ala Pro Ile Ala Lys Thr Ile Ser Lys Ala Lys Gly
    210                 215             220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 81
<211> LENGTH: 13
<212> TYPE: PRT
<213> ORGANISM: Artificial
<220> FEATURE:
<223> OTHER INFORMATION: HVR-H3 of control antibody 11-x

<400> SEQUENCE: 81

Ala Arg Ala Thr Thr Val Val Gly Thr Asp Phe Asp Tyr
1               5                   10
```